United States Patent
Cushing et al.

(10) Patent No.: US 9,339,649 B2
(45) Date of Patent: May 17, 2016

(54) IMPLANTABLE COCHLEAR SYSTEMS WITH INTRACOCHLEAR ELECTRODE ARRAY FOR BALANCE STABILIZATION

(71) Applicants: THE HOSPITAL FOR SICK CHILDREN, Toronto (CA); UNIVERSITY HEALTH NETWORK, Toronto (CA)

(72) Inventors: Sharon Cushing, Toronto (CA); Blake Papsin, Toronto (CA); David Pothier, Toronto (CA); Cian Hughes, Dublin (IE)

(73) Assignees: The Hospital for Sick Children, Toronto (CA); University Health Network, Toronto (CA)

( * ) Notice: Subject to any disclaimer, the term of this patent is extended or adjusted under 35 U.S.C. 154(b) by 0 days.

(21) Appl. No.: 14/384,610

(22) PCT Filed: Mar. 12, 2013

(86) PCT No.: PCT/CA2013/050184
§ 371 (c)(1),
(2) Date: Sep. 11, 2014

(87) PCT Pub. No.: WO2013/134873
PCT Pub. Date: Sep. 19, 2013

(65) Prior Publication Data
US 2015/0032186 A1 Jan. 29, 2015

Related U.S. Application Data

(60) Provisional application No. 61/609,672, filed on Mar. 12, 2012.

(51) Int. Cl.
*A61N 1/36* (2006.01)

(52) U.S. Cl.
CPC .................... *A61N 1/36032* (2013.01)

(58) Field of Classification Search
None
See application file for complete search history.

(56) References Cited

U.S. PATENT DOCUMENTS

| 5,095,904 A | 3/1992 | Seligman et al. |
| 5,719,528 A | 2/1998 | Rasmussen et al. |

(Continued)

FOREIGN PATENT DOCUMENTS

WO 02/05590 1/2002

OTHER PUBLICATIONS

Roehm et al., "Isolation of Transtympanic Characteristics Utilizing a High-Definition Video Otoscope at Individual Visible Light Frequencies", Otolaryngology—Head and Neck Surgery, Aug. 2011, vol. 145, p. 96.

(Continued)

*Primary Examiner* — Kennedy Schaetzle
(74) *Attorney, Agent, or Firm* — Geoffrey deKleine; Borden Ladner Gervais LLP

(57) ABSTRACT

A system for rehabilitating patients affected by balance disorders with or without vestibular hypofunction and/or malfunction with or without an associated hearing loss, which includes sensors of sound and head movement, processing circuitry, a power source coupled to head phones, an air conduction hearing aid, bone conduction hearing aid, middle ear implant or an electrical stimulator implanted into the cochlea capable of stimulating areas within the cochlea with the potential for current spread to surrounding non-auditory areas including the vestibular system.

13 Claims, 19 Drawing Sheets

(56) References Cited

U.S. PATENT DOCUMENTS

| | | |
|---|---|---|
| 5,919,149 A | 7/1999 | Allum |
| 6,063,046 A | 5/2000 | Allum |
| 6,546,291 B2 | 4/2003 | Merfeld et al. |
| 7,225,028 B2 | 5/2007 | Della Santina et al. |
| 7,647,120 B2 | 1/2010 | Della Santina et al. |
| 7,867,140 B2 | 1/2011 | Chiari et al. |
| 2007/0038268 A1 | 2/2007 | Weinberg et al. |
| 2007/0208403 A1 | 9/2007 | Della Santina et al. |
| 2007/0249889 A1* | 10/2007 | Hanson et al. .................. 600/25 |
| 2009/0247813 A1 | 10/2009 | Parker |
| 2012/0022616 A1 | 1/2012 | Garnham et al. |
| 2012/0277835 A1* | 11/2012 | Della Santina et al. ......... 607/62 |

OTHER PUBLICATIONS

Extended European Search Report issued in respect European Patent Application No. 13761435.0 on Oct. 21, 2015.

* cited by examiner

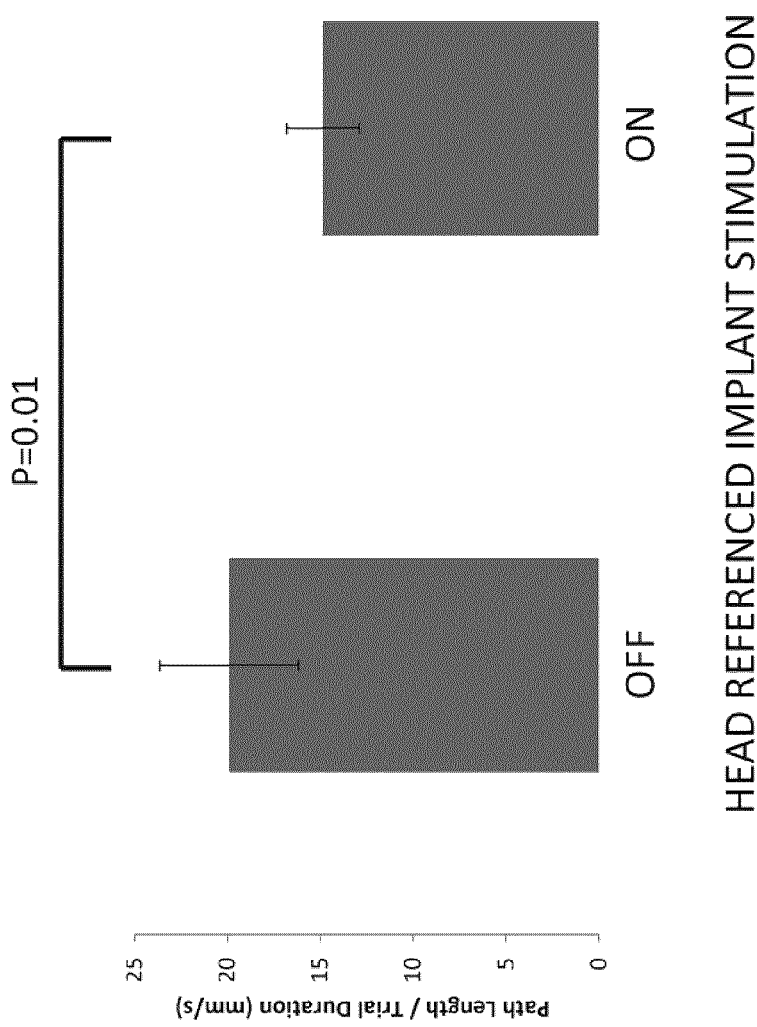

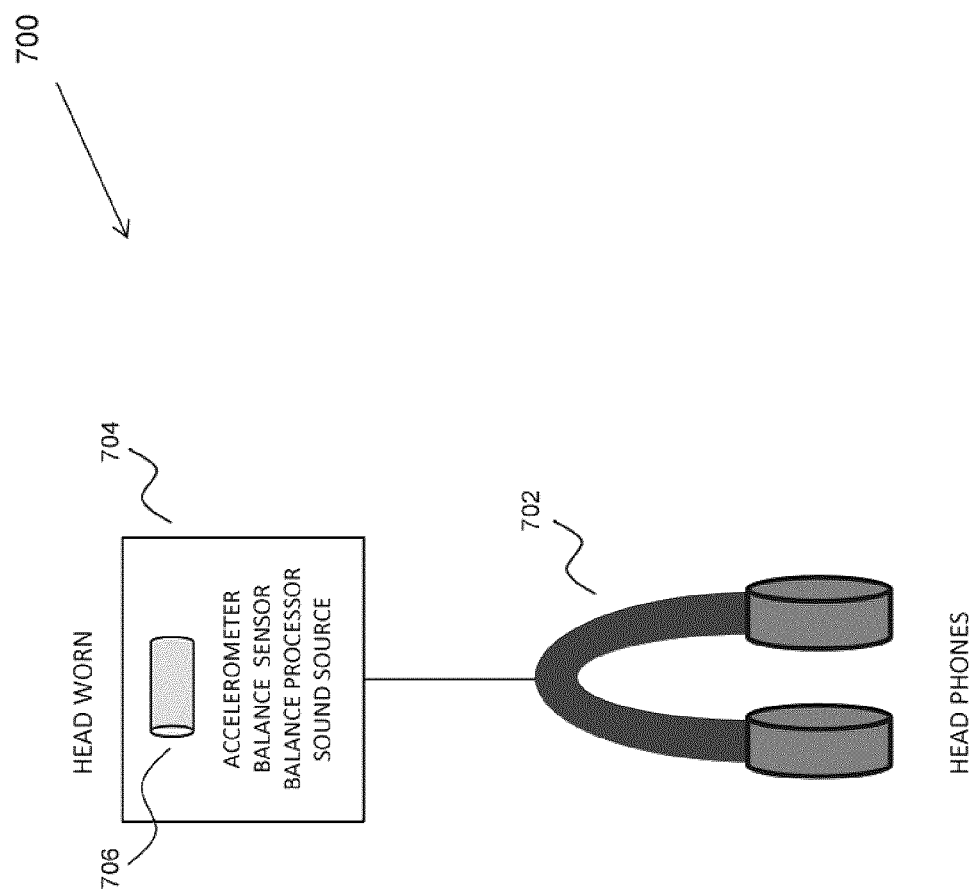

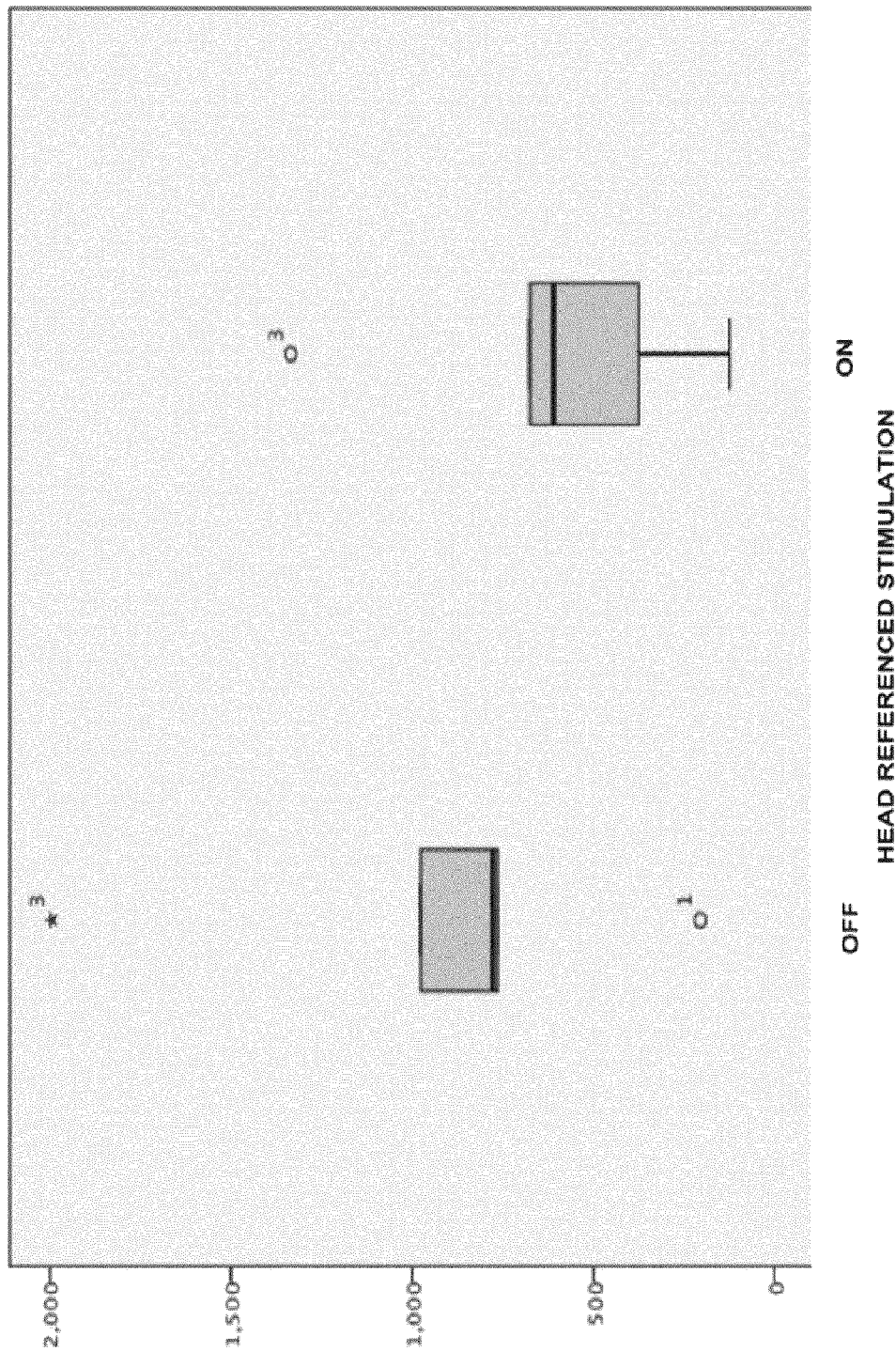

IMPLANTABLE COCHLEAR SYSTEMS WITH INTRACOCHLEAR ELECTRODE ARRAY FOR BALANCE STABILIZATION

CROSS-REFERENCE

This application is a national entry of PCT/CA2013/050184 filed Mar. 12, 2013, which claims the benefit of and priority to U.S. Provisional Patent Application No. 61/609,672 filed Mar. 12, 2012.

FIELD

The embodiments described herein relate to a system for treating patients suffering from balance disturbance and, at times, hearing loss. Various embodiments disclosed herein relate to, air conduction and bone-anchored hearing aid as well as middle ear or cochlear implant systems and methods.

BACKGROUND

Vestibular sensory loss can cause a person to suffer from impaired balance function. Vestibular sensory loss can be accompanied by cochlear sensory loss which is one possible cause of hearing loss. Such deficits may result from cochlear and/or, vestibular end-organ dysfunction.

SUMMARY

In a first aspect, the present disclosure provides a stimulation system. In various embodiments, the system comprises; an implantable cochlear stimulator; at least one microphone configured to sense and provides audio information; at least one balance sensor configured to sense and provides balance information; and at least one processor configured to generate control signals in response to the audio information provided by the at least one microphone and the balance information provided by the at least one balance sensor. In various embodiments, the cochlear stimulator comprises: a pulse generator that generates electrical stimulation pulses as defined by control signals; and an electrode array adapted to be inserted into a patient's cochlea and provide electrical stimulation pulses to the patient's auditory nerve based on the control signals.

In various embodiments, the balance sensor is head-referenced. In some embodiments, the balance sensor is adapted to be implanted into the patient's skull.

In various embodiments, the electrical stimulation pulses comprise audio stimulation pulses based on the audio information and balance stimulation pulses based on balance information.

In various embodiments, the balance stimulation pulses are steered towards the patient's vestibular nerve/end-organs/neural elements. In some embodiments, the balance stimulation pulses are steered towards the patient's facial nerve.

In some embodiments, the at least one processor is configured to generate control signals for steering the balance stimulation pulses towards the patient's vestibular nerve/end-organs/neural elements. In some embodiments, the at least one processor is configured to generate control signals for steering the balance stimulation pulses towards the patient's facial nerve.

In some embodiments, the at least one processor, when in use, is external to the patient.

In some embodiments, the at least one balance sensor, when in use, is external to the patient.

In some embodiments, the at least one balance sensor is directly coupled to at least one processor.

In some embodiments, at least one balance sensor is coupled to at least one processor through a wired limb.

In some embodiments, at least one balance sensor is wirelessly coupled to at least one processor.

In some embodiments, at least one processor is wirelessly coupled to the implantable cochlear stimulator.

In some embodiments, the balance sensor is mounted within at least one processor.

In some embodiments, the balance sensor comprises a motion sensor, an accelerometer, a gyroscope, a position sensor, an orientation sensor, or any combination of the foregoing. For example, in various embodiments, the motion sensor comprises gyro-stabilized accelerometers for provicing balance biofeedback.

In another aspect, the present disclosure provides a method of treating hearing loss and balance disorders comprising: sensing audio information; sensing balance information; and providing electrical stimulation pulses to the patients auditory nerve based on sensed audio information and balance information.

In some embodiments, the electrical stimulation pulses are provided in proximity to the cochlear nerve.

In some embodiments, the electrical stimulation pulses are provided at the cochlear nerve.

In some embodiments, the electrical stimulation pulses comprise audio stimulation pulses based on the audio information and balance stimulation pulses based on balance information.

In some embodiments, the balance stimulation pulses are steered towards the vestibular nerve/end-organs/neural elements.

In some embodiments, the balance stimulation pulses are steered towards the facial nerve.

In another aspect, the present disclosure provides a method of treating balance disorders comprising: sensing balance information; and indirectly stimulating the vestibular system by providing electrical stimulation pulses in proximity to the cochlear nerve based on the sensed balance information.

In some embodiments, the electrical stimulation pulses are provided at the cochlear nerve.

In another aspect, the present disclosure provides a stimulation system comprising: an implantable cochlear stimulator; at least one balance sensor configured to sense and provide balance information; and at least one processor configured to generate control signals in response to the balance information provided by the at least one balance sensor, and to provide the control signals to the implantable cochlear stimulator. In various embodiments, the cochlear stimulator comprises a pulse generator that generates electrical stimulation pulses as defined by control signals; and an electrode array adapted to be inserted into a patient's cochlea and provide electrical stimulation pulses to the patient's auditory nerve based on the control signals In some embodiments, the balance sensor is head-referenced.

In some embodiments, the balance sensor is adapted to be implanted into the patient's skull.

In some embodiments, the electrical stimulation pulses balance stimulation pulses based on balance information.

In some embodiments, the balance stimulation pulses are steered towards the patient's vestibular nerve/end-organs/neural elements.

In some embodiments, the balance stimulation pulses are steered towards the patient's facial nerve.

In some embodiments, the at least one processor is configured to generate control signals for steering the balance stimulation pulses towards the patient's vestibular nerve/end-organs/neural elements.

In some embodiments, the at least one processor, when in use, is external to the patient.

In some embodiments, the at least one balance sensor, when in use, is external to the patient.

In various embodiments, the at least one balance sensor is coupled to at least one processor directly, through a wired limb, or wirelessly.

In some embodiments, at least one processor is wirelessly coupled to the implantable cochlear stimulator.

In some embodiments, the balance sensor is mounted within at least one processor.

In some embodiments, the balance sensor comprises a motion sensor, an accelerometer, a gyroscope, a position sensor, an orientation sensor, or any combination of the foregoing. For example, in various embodiments, the motion sensor comprises gyro-stabilized accelerometers for provicing balance biofeedback.

In another aspect, the present disclosure provides a stimulation system comprising: at least one balance sensor configured to sense and provide balance information; a stimulator for providing a stimulation to a patient; and a processor configured to providing control signals to the transducer based on the balance information.

In some embodiments, the balance sensor is head-referenced.

In some embodiments, the balance sensor is adapted to be implanted in a patient's skull.

In some embodiments, the stimulator comprises an electrode array adapted to be inserted into a patient's cochlea.

In some embodiments, the stimulator comprises a transducer. In some embodiments, the transducer comprises an electroacoustic transducer, an electromechanical transducer, one or more skin-surface electrodes, or a combination thereof.

In various embodiments, the transducer is incorporated in headphones or a hearing aid.

In another aspect, the present disclosure provides a balance disorder, the method comprising: determining whether a position of a head has exceeded an anterior limit, a posterior limit, a left limit and a right limit; providing a first stimulation if the head has exceeded the anterior limit, providing a second stimulation if the head has exceeded the posterior limit; providing a third stimulation if the head has exceeded the left limit; and providing a fourth stimulation if the head has exceeded the right limit.

In various embodiments, the first, second, third and fourth stimulations comprise auditory stimulations, auditory percepts, or vestibular stimulation. In some embodiments, the first, second, third and fourth stimulations are not perceptible to the patient.

In some embodiments, no stimulus is provided if none of the limits are exceeded.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures, in which:

FIG. 6A illustrates boxplots of path length values for posturography tests;

FIG. 7 illustrates a stimulation system according to various embodiments;

FIG. 9A illustrates boxplots of path length values for posturography tests;

DETAILED DESCRIPTION

Figure 1:
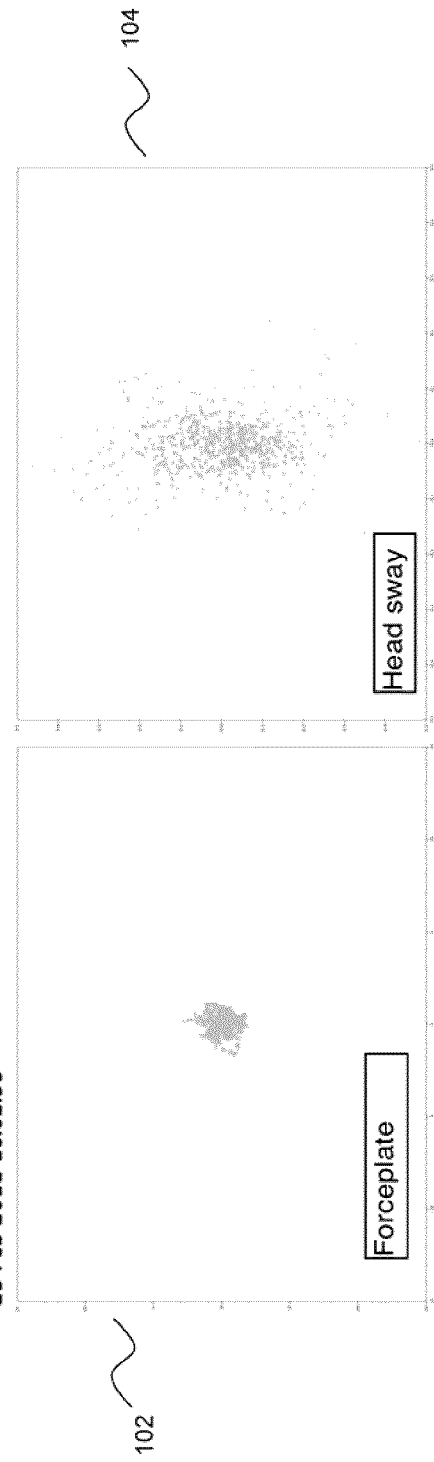
FIG. 1 illustrates two sets of balance data, specifically foot and head position, synchronously obtained based on a force plate and head tracker.

Vestibular loss, particularly when bilateral and coupled with loss of other sensory modalities (e.g. vision, proprioception, hearing) is known to cause deficiencies in balance. Poor balance can lead to difficulties with ambulation, frequent falls and thus presents significant safety concerns. Given the degree of their impairment, individuals who display such difficulties with balance are eager to have a treatment or device that would yield stability. A number of groups have examined the use of sensory biofeedback in an effort to improve postural stability in these patients (e.g., in U.S. Pat. Nos. 8,092,398, 6,546,291 and 7,867,140). These devices typically consist of at least one motion sensor coupled to at least one part of the body, processing and acquisition systems that encode the signal from the motion sensor and a form of sensory output that is delivered to the patient. In their various descriptions, the sensory output can include stereophonic sound, vibrotactile feedback, electromechanical vibration, visual feedback or even electrical stimuli. While these devices do provide feedback about body position sense that is useful in the maintenance of balance, they have a number of limitations. Such deficits may result from cochlear and/or, vestibular end-organ dysfunction. Some known systems address balance impairment using external motion sensors coupled to a sensory feedback signal. Other known systems more specifically address the vestibular loss alone by providing an electrode array that is implanted at the vestibular nerve of a patient and provides direct electrical stimulation to the vestibular nerve, end-organs or neural elements. Other known systems address cochlear sensory loss alone by providing an electrode array to deliver direct electrical signals to the cochlear nerve. Other known systems address both cochlear and vestibular sensory loss by providing one electrode array to deliver electrical signals directly to the cochlear nerve and a second separate electrode array that is implanted at the vestibular nerve of a patient to provide direct electrical signals to the vestibular nerve/end-organs/neural elements.

Some embodiments described herein relate to a novel device that includes the coupling of head position via balance sensors with modulated sensory feedback that can be incorporated with some of the technology described in some of the above patents with a number of improvements and additions that address these limitations in an effort to achieve improved postural stability. Some of the novel elements of some of the embodiments described herein include 1) the way in which motion and orientation is referenced (e.g., motion and orientation sensors referenced to the plane of at least one of the vestibular end-organs) 2) the way in which motion and position is recorded (e.g. feedback of both head position relative to the plane and also position in space) and 3) the way in which the sensory stimulus is provided in response to the motion and orientation sensor (e.g. provision of a 'silent' (e.g. no stimulus) zone). It should be understood that the term 'silent' does not necessarily imply the use of an auditory stimulus. Some embodiments described herein may include mechanisms to calibrate or re-calibrated during normal use such that the device can consistently provide feedback to the user in different orientations and when placed on various body parts. Not all embodiments include each of these features. Some embodiments may not include any of these features. Some embodiments include all of these features. Various embodiments may include other novel features described herein.

Some embodiments include at least one balance sensor that is head mounted in the plane of at least one of the vestibular end-organs (as used herein, the term "head mounted" can include ear mounted). For example, when mounted in the plane of the macula of the utricles, the sensor detects changes in head orientation in a similar fashion to the utricle, the peripheral vestibular end-organ that provides most vestibular data to the brain for the maintenance of upright balance. A utricle-referenced system allows for a more precise estimation of head tilt given its proximity to this vestibular end-organ. This is of considerable importance as the vestibular system resides within the head and biofeedback of balance is likely to be best if delivered in response to head movements as opposed to other parts of the body commonly used in other biofeedback systems.

Figure 2:
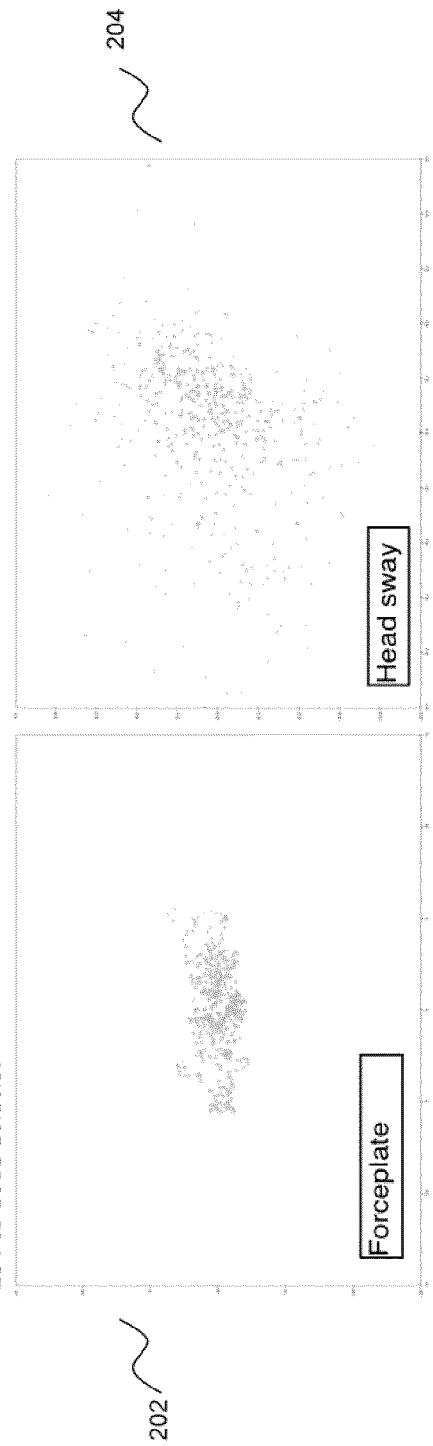
FIG. 2 illustrates two sets of balance data, specifically foot and head position, synchronously obtained based on a force plate and head tracker.
Figure 3:
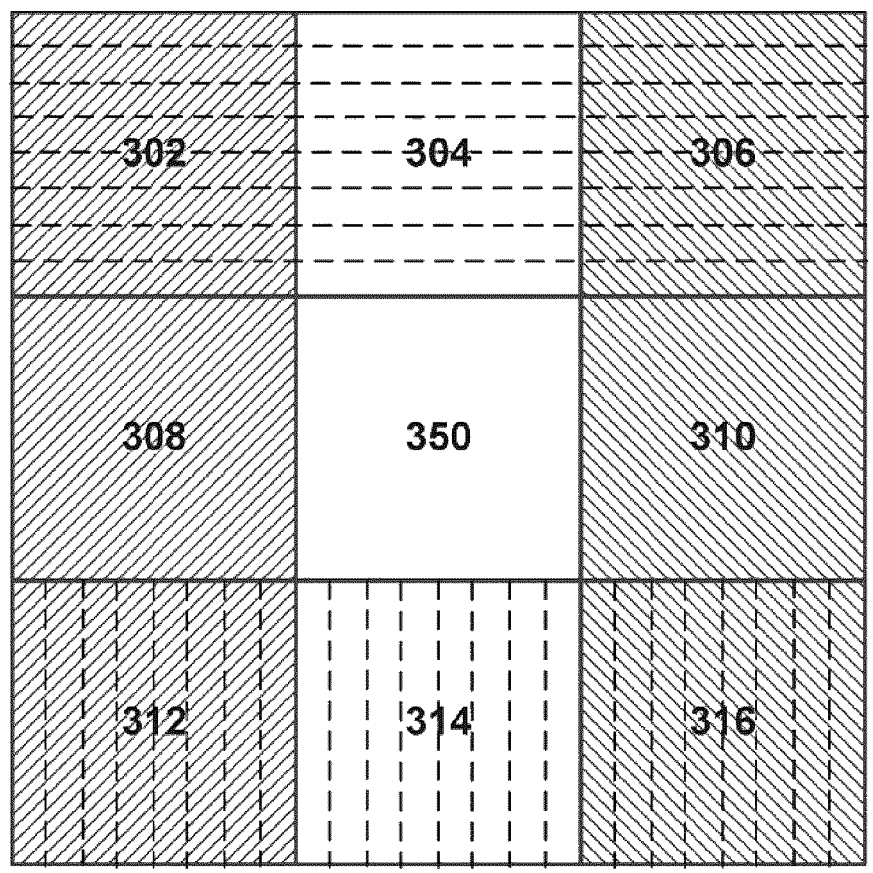
FIG. 3 illustrates a diagram that outlines the stimulus-free limits for head movement and corresponding stimulation provided when a limit is exceeded according to various embodiments.

Following from this and owing to the fact that head movements have been difficult to measure in a clinical context, there are little data available on the importance of head movement in the diagnosis and monitoring of balance disorders. This can be shown by data recorded from normal human controls and with patients with vestibular lesions. FIGS. 1 and 2 show a comparison of data derived from centre of pressure (COP) measurements measured by a force plate underfoot and head movement in a synchronized fashion. FIG. 3 of U.S. Pat. No. 8,092,398, describes the mechanism by which standard accelerometer based devices measure sway. In such known systems, the body is measured as a single system; this is, however, not the case from a physiological point of yew. The body can tilt at the ankles, hips and neck. Using standard accelerometer based measurement for biofeedback will allow parts of this multi-level system to be measured, but unless the head is measured in a similar fashion to the way it is measured by the utricle, important information is lost. This stands to reason as the normal body physiology involves the vestibular system that is located within the skull. This can also be shown where synchronized measurements are made of centre of pressure (analogous to standard accelerometer-based units) and head measurements that incorporate roll, pitch and yaw. FIGS. 1 and 2 show this difference for a patient with bilateral vestibular lesions under a variety of balance conditions. FIG. 1 corresponds to a patient standing on a firm surface and FIG. 2 corresponds to a compliant surface, such as foam. Graph 102 of FIG. 1 shows the force plate measurements while graph 104 shows the head sway measurements. The measurements in graphs 102 and 104 are synchronized. Similarly, graph 202 of FIG. 2 shows the force plate measurements while graph 204 shows the head sway measurements. The measurements in graphs 202 and 204 are synchronized.

It is important to understand that the vestibular system is located in the petrous bone of the skull and that this is the ideal situation for an organ that needs to detect angular and linear movements/accelerations in all three Cartesian planes. Head stabilization is key to balance and as the vestibular end-organs are coupled with the skull, a device (e.g. a balance sensor) coupled to the skull (as opposed to a different part of the body) will be better suited to measure the effects a body movement in a fashion similar to the vestibular system.

The novel combination of balance sensors (e.g. accelerometers and gyroscopes) in some of the described embodiments allows them to match and detect head movement in a similar manner as that undertaken in the physiological vestibular system. This unique combination of accelerometers and gyroscopes provide linear acceleration information as well as angular acceleration in all three Cartesian planes. Given the combination of balance sensors used (which in some embodiments include gyroscopes and accelerometers or gyro-stabilised accelerometers), various embodiments of the device can detect movements and also determine the relative position of the device in three dimensions at all times rather than merely measuring movements, something not possible with existing devices. Using a combination of balance sensors (which in some embodiments include accelerometers and gyroscopes) allows a more physiological measurement of head movement and more importantly, head position. Previously described devices cannot accomplish this. This innovation mimics the functioning vestibular system that uses a combination of the same principles. The semi-circular canals detect angular acceleration but, although they maintain a regular neuronal firing rate, they cannot easily detect final position relative to starting position; this is one of the reasons that the balance system functions as a combination of semicircular canals and the otolith organs. The utricle and saccule (the otolith organs) detect linear movements and function in conjunction with the semi-circular canals produce a gyroscopic effect. This is reproduced by some of the embodiments described herein.

By combining balance sensor data (e.g. accelerometry and gyroscopic data), some embodiments can determine the difference between acceleration due to intentional movements (e.g. looking down) and acceleration due to the sway of imbalance (e.g. falling forward). In various embodiments this ability is tied to the fact that some embodiments are able to measure acceleration towards gravity in a fixed plane of the device (e.g. altitude). In some embodiments this is done through the use of a specific computational algorithm and information from a single accelerometer source. By analysing both data streams with a real time decision making system, some embodiments can determine when it is (e.g. falling forward) and is not (e.g. looking down) necessary to provide biofeedback to reorient the patient. By minimising the biofeedback provided some embodiments can optimise the patient response to this feedback.

Figure 4:
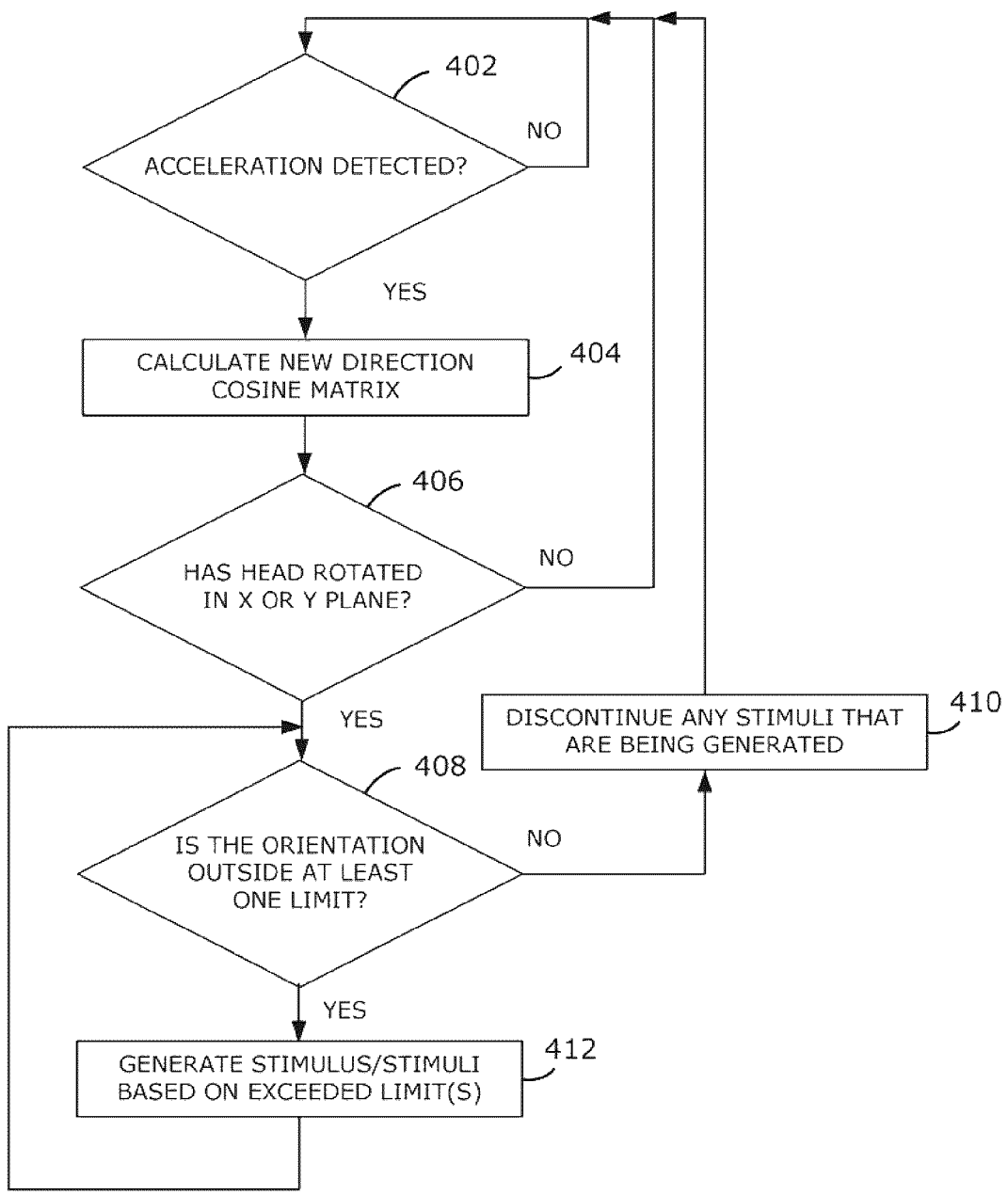
FIG. 4 outlines an activation pathway and decision making method embodied in the stimulation device.

In the example of a utricle-referenced position of the device, movements affecting the lateral semicircular canal, which lies in an almost identical plane, can be measured. This configuration provides the ability to measure movement relative to gravity (attitude). As outlined above, by relating change in sensor orientation to change in altitude it is possible to differentiate between an isolated movement such as tilting the head forward with no body sway, and a change that represents a patient falling. FIG. 4, which is described in detail below, outlines the activation pathway and decision making method embodied in the stimulation device.

A problem with biofeedback (e.g. auditory or otherwise) utilized in other devices is that when constant tones are used to supply feedback regarding position, there is no point at which no sound is delivered. This constant sound can be likened to tinnitus, which is known to be extremely bothersome to patents. In addition, if you have a continuous auditory sweep from front to back (e.g. no silent zone), unless patients have perfect pitch they will not be able to easily distinguish the target upright position. The target location/posture is not obvious in this scenario. Some of the described embodiments deliver single tones or broadband clicks as feedback when a threshold of tilt, roll or yaw is achieved. By adjusting these parameters, an area called a 'sweet spot' is produced where no sensory stimulus delivered, in this case, sound is not heard when the patient is standing upright with a correct posture; Since in some embodiments disclosed herein, measurements are in three axis, the sweet spot can be either two or three dimensional. Its size and shape can be also be customized for a particular patient, deficit or activity. FIG. 3 described below illustrates the use of thresholds and "sweet spot".

Biofeedback requires, at minimum a signal to be delivered when limits are exceeded in an anterio-posterior (AP) and in a left-right (LR) direction. Various embodiments disclosed herein relate to a novel technique to overcome the difficulty of providing a range of stimuli to achieve this. Some embodiments produce broadband clicks (delivered to the ear in question) when the head rolls to the side. This provides LR data without interfering with the pure tone delivery binaurally for AP movements. AP movements can be discriminated by two distinct pure tones (e.g. 880 Hz and 220 Hz) for anterior and posterior movements, respectively. Owing to the existence of the 'sweet spot', these can be delivered as discrete stimuli at a single amplitude. We have shown that a stepped or linear delivery of stimuli add nothing to the effect as our study subjects used the edges of the sweet spot to reference their position, seldom swaying to an area where there would be a change of output when stepped or linear output are used.

FIG. 3 illustrates a possible grid 300 to be used in conjunction with the sound playback described above. The grid 300 in FIG. 3 illustrates various sectors of possible head position along with possible stimuli assignments to each of the sectors. As described above, depending on the head position different stimuli are delivered to the user. If the individual's head moves to a sector including the pattern designated as 360, broadband clicks will be delivered in their left ear. If the individual's head moves to a sector including the pattern designated as 370, broadband clicks will be delivered in their right ear. If the individual's head moves to a sector including the pattern designated as 380, an 880 Hz tone will be delivered to both ears. If the individual's head moves to a sector including the pattern designated as 390, a 220 Hz tone will play in both ears. For example, in sector 306, both broadband clicks to the right ear and an 880 Hz tone to both ears will be played. In contrast, in sector 310, only broadband clicks to the right year are played. In each of sectors 304, 308, 310, and 314, only one type of stimulus is delivered. In each of sectors 302, 306, 312, and 316, two types of stimuli will be delivered. Sector 350 represents the "sweet spot" where no stimuli are delivered.

In some embodiments, the determination of whether the head moves to a particular sector takes into account the position and/or movement of the head relative to the rest of the body. Accordingly, in some embodiments, a determination that the head is in sector 308 indicates that the head has swayed to the left and not that the individual has stepped laterally to the left.

In some embodiments, the 'sweet spot' may be rectangular, elliptical or otherwise shaped such that the anterior, posterior, right and left limits may not be equal.

In some embodiments, the 'sweet spot' may adjust dynamically in response to the movement of the device and/or user, such that the size and shape of the 'sweet spot' may vary with time, location, orientation, or due to other measured or user generated input.

In some embodiments, if a patient's head exceeds two of the limits, then the corresponding stimuli for each of the limits will be generated. Accordingly, in various embodiments, the stimulus parameters are selected so as not to interfere with one another. For example, in some embodiments a tone is used for the anterior limit and a click is used for the right limit. Accordingly, if the patient's head were to exceed both the anterior and right limit (which corresponds to the upper-right section of FIG. 3), then both clicks to the right ear and a 880 Hz tone to both ears would be generated. In some embodiments, these stimuli when played together will be distinguishable such that a patient can determine which limits have been exceeded.

It should be understood that the stimulus parameters described herein are examples only and are not intended to be limiting. In particular, various embodiments can use other stimulus parameters or the same stimulus parameters but assigned to other directions. It should be understood that the stimuli provided are in some embodiments are perceptible to the patient (e.g. biofeedback) however perceptibility of the provided stimulus is not a requirement of all embodiments disclosed herein. More specifically, in some embodiments, the stimuli that are provided are not perceptible to the patient. Some such embodiments include providing stimuli to the vestibular nerve.

In summary, signals generated by the device can be used to provide feedback to any of the sensory organs. Sound and vibrotactile outputs are the most easily used however other modalities including but not limited to vision, galvanic vestibular stimulation/transcutaneous electro-vestibular stimulation, as well as stimulation provided by an intracochlear electrode array (e.g. cochlear implant) for example could be used. Signals can be sent directly to the ear through headphones, but can also be coupled to, air conduction hearing aids, bone-anchored hearing aids, middle ear and cochlear implants as well as other devices. This coupling will be described in further detail below.

A flowchart illustrating an example of a method of the activation pathway and decision making carried out by a stimulation system, such as for example stimulation systems 700, 1000, 1100, 1200, 1300, 1400, 1500, and 1600 is shown in FIG. 4. The method may be carried out by software executed by, for example, the balance and/or speech processors of the stimulation systems 700, 1000, 1100, 1200, 1300, 1400, 1500, and 1600. Coding of software for carrying out such a method is within the scope of a person of ordinary skill in the art given the present description. The method may contain additional or fewer processes than shown and/or described, and may be performed in a different order. Computer-readable code executable by at least one controller or processor of the portable electronic device to perform the method may be stored in a computer-readable medium, such as a non-transitory computer-readable medium.

At 402, it is determined whether an acceleration has been detected. If an acceleration has not been detected, then 402 is repeated. If an acceleration has been detected at 402, then the method continues to 404.

At 404, a new direction cosine matrix is calculated, which is a measure of the orientation of the device relative to the unit vectors x, y, and z. In some embodiments, 404 comprises calculating a roll, pitch and yaw.

At 406, it is determined whether the head has rotated in the x or y plane. If the head has not rotated in the x or y plane, then the acceleration is linear acceleration only. This is indicative of an intentional movement, such as for example but not limited to, looking down. Accordingly, if the head has not rotated, then the method continues to monitor the acceleration by repeating 402. In contrast, if the head has rotated in the x or y plane, then this can be indicative of an unintentional movement and the method continues to 408.

At 408, it is determined whether the orientation of the body is outside the predetermined limits, which can be for example, the limits illustrated in FIG. 3. If the orientation is not outside the limits, then the method continues to 410. If at least one limit has been exceeded, then method continues to 412.

At 410, any stimuli that are being generated are discontinued because it was determined at 408 that none of the limits are exceeded. After 410, the method continues to monitor acceleration at 402.

At 412, a stimulus or stimuli is/are generated based on which limit(s) has/have been exceeded. The number of limits that are used can depend on the shape of the "sweet spot" and how the limits are assigned. As explained above, the sweet spot can be rectangular or square, in which case each side of the sweet spot may be designated as a limit. If each side of the square is a limit, then two limits can be exceeded at a time. In other embodiments, the perimeter of the sweet spot may be divided into an arbitrary number of limits each of which may or may not overlap with another limit. For example, in the case of an ellipse, the perimeter the ellipse may be divided into any number of limits, which may overlap.

In some embodiments, sound stimuli are generated such as, for example, those discussed above with reference to FIG. 3. In other embodiments, other stimuli may be used such as for example, but not limited to, visual stimuli, tactile stimuli, as well as other types of stimuli mentioned in the present disclosure. Some embodiments utilize a combination of different types of stimuli, such as for example, but not limited to, sound and visual stimuli. Once 412 has been executed, the method repeats 408.

It should be understood that 412 also includes discontinuing any stimulus that corresponds to a limit that is no longer exceeded. For example, in a first iteration, it may have been determined at 408 that two limits were exceeded. Accordingly, in the first iteration, two stimuli were generated at 412. At the second iteration of 408, one of the limits may no longer be exceeded while the second limit may still be exceeded. Accordingly, at the second iteration of 412, one of the stimuli would be discontinued while the second stimulus would continue.

Cochlear and vestibular sensory loss frequently occur together, because the hearing and balance end-organs that make up the two parts of the inner ear are similarly sensitive to the insults that lead to hearing loss (e.g. infection (meningitis), genetic mutations etc.). A number of standard commercial devices are utilized to rehabilitate hearing loss. For example, depending on the severity and nature of the hearing loss, traditional hearing aids, bone conduction hearing aids, middle ear implants (e.g. fixed to ossicular chain, round window) and cochlear implants can be used. The term "bone conduction hearing aids" as used herein includes, but is not limited to, active and passive, as well as adhesive, headband retained, percutaneous bone anchored and transcutaneous magnet retained bone conduction hearing aids. Various embodiments described above can make use of any such devices for example coupling to such devices via either direct cable connection, WiFi (IEEE 802.11), Bluetooth (IEEE 802.15), ZigBee (IEEE 802.15.4) or other wireless connection. In the setting of air conduction hearing aids, bone conduction hearing aids and middle ear implants, some embodiments would provide amplified auditory or other sensory cues in response to head referenced motion. In addition to the provision of auditory cues, coupling of head referenced low frequency sound in particular via a bone-anchored hearing aid would provide a reliable vibrotactile signal. Further description of the coupling with cochlear implants specifically and the implications for this population are outlined below.

Some currently available cochlear implants can restore auditory sensation and preliminary evidence suggests that the restoration of hearing in and of itself may yield a positive effect on balance function).[1, 2] However, balance function remains poor in a large proportion of individuals requiring cochlear implants even following cochlear implantation. The poorest function is seen in those individuals with concurrent loss or dysfunction of their vestibular end-organs, however balance dysfunction is also seen in some patients where vestibular end-organ function is normal. Research has shown that greater than 50% of children with profound sensorineural hearing loss have an associated vestibular deficit.[2-5] Beyond the restoration of hearing through cochlear implantation, there are currently no effective therapeutic options for these individuals with significant balance dysfunction. The disability that results from poor balance function, with and without associated vestibular loss, is variable. In children specifically, poor balance leads to delay in attaining motor milestones and challenges in acquiring advanced motor skills (e.g. riding a bike without training wheels). These children have frequent falls and often undergo intensive physical therapy aimed at improving their balance skills. Recent data suggests that vestibular loss in children with cochlear implants may put them at increased risk of implant failure from frequent head trauma.

Many of the known cochlear implant systems currently available provide significant benefits to patients who wish to hear. Presently available implantable stimulation devices, typically have an implanted unit, an external AC coil and an external control unit and power source. The external control unit and power source includes a suitable control processor and other circuitry that generates and sends the appropriate command and power signals to the implanted unit to enable it to carry out its intended function. The external control unit and power source are powered by a battery that supplies electrical power through the AC coil to the implanted unit via inductive coupling for providing power for any necessary signal processing and control circuitry and for electrically stimulating select nerves or muscles. Efficient power transmission through a patient's skin from the external unit to the implanted unit via inductive coupling can be achieved through constant close alignment between the two units.

As previously mentioned, a significant percentage (>50%) of these patients implanted with cochlear stimulation systems suffer from balance deficiencies, some of which originate in the vestibular system.[2-5] Recently, others have attempted to treat balance deficiencies through a variety of different modalities, including stimulating the vestibular system. Single-modality vestibular prostheses (e.g., in U.S. Pat. No.

6,546,291) exist and provide artificial vestibular sensation, however these devices do not address the associated hearing loss. Examples of vestibular stimulation systems are taught in U.S. Pat. No. 6,546,291 (the '291 patent); U.S. Pat. No. 6,219,578 (the '578 patent); U.S. Pat. No. 6,063,046 (the '046 patent); and U.S. Pat. No. 5,919,149 (the '149 patent); and dual cochlear/vestibular stimulation systems are taught in U.S. Pat. No. 7,225,028 (the '028 patent) and U.S. Pat. No. 7,647,120 (the '120 patent), all of which are incorporated herein by reference in their entireties. In general, each document that is incorporated in this disclosure is incorporated in its entirety.

In the '291 patent issued on Apr. 8, 2003. Merfeld, et al, teach a balance prosthesis that provides information indicative of a patient's spatial orientation to the patient's nervous system. This is done by placing 3 rotational accelerometers in mutually orthogonal cardinal X Y Z planes to measure roll, pitch and yaw of the head (see, '291 Merfeld patent at column 4 line 35). In the '578 patent issued on Apr. 17, 2001, Collins, et al, teach transcutaneous electrical of the vestibular system in order to modify a patient's postural sway. In the '046 patent issued on May 16, 2000, Allum teaches a method and apparatus for the diagnosis of abnormal human balance corrections. And, in the '149 patent issued on Jul. 6, 1999, Allum teaches a method and apparatus for the diagnosis and rehabilitation abnormal human postural sway. As exemplified above, there are systems for treating hearing deficiencies and balance deficiencies separately. Given this deficiency, a single system aimed at simultaneously treating patients with both hearing and balance deficiencies was needed. With this in mind, in the '028 patent issued May 29, 2007 to Della Santina et al. proposed a dual cochlear/vestibular stimulator aimed at restoring combined cochleovestibular losses. This device functions by selectively stimulating all branches of the auditory-vestibular nerve with the aim of restoring hearing and normalizing gaze- and posture-stabilizing reflexes and perception of spatial orientation. To work however this device requires the insertion of an internal stimulation device and therefore is not applicable to the over 200 000 individuals who already have cochlear implant devices in place, many bilaterally. Incorporation of this type of new technology would require surgical removal or updating of the old device or waiting for that device to fail which could take upwards of a decade. While the ability to selectively and independently stimulate the cochlear and vestibular systems may be advantageous in some instances, the decision to implant such devices requires that accurate methods for assessing vestibular function be available. Children make up a large proportion of cochlear implant recipients and in the setting of congenital deafness, infants are routinely implanted bilaterally at less than a year of age. It can be challenging to ascertain at this age whether or not these children have intact vestibular function. Knowing the function of the underlying vestibular end-organs would however be crucial in deciding whether or not to implant a traditional cochlear implant device versus a known hybrid cochlear/vestibular stimulating device. Likewise the hybrid cochlear/vestibular stimulating device would not address balance dysfunction that occurs in many individuals with hearing loss in the presence of intact vestibular end-organ function. Review of the currently available systems aimed at addressing combined cochlear/vestibular dysfunction and balance problems highlights the advantages and need for an external device/processor that could be applied or "retrofit" to a currently implanted cochlear electrode array. Such a device as described above would contain the ability to sense motion. The information provided by the balance sensor could then be encoded and could lead to selected activation of the electrode array. Activation of the electrode array would then lead to an auditory percept that is head referenced and meaningful to balance.

While using auditory or other sensory cues referenced to head position are known to lead to balance stabilization, an improved system would promote balance more directly through direct stimulation of the vestibular end-organs/nerve as described for example in '028 patent issued May 29, 2007 to Della Cantina et al. As outlined above this device contains a separate electrode array for stimulation of the vestibular end-organ/nerve and that carries with it a number of limitations that were outlined above.

We suggest that a small portion of the electrical current derived from an intra-cochlear electrode array (e.g. cochlear implant) intended for the cochlea to facilitate hearing could rather be steered to either directly or indirectly stimulate the vestibular end-organs/nerve and, more importantly, promote stability by providing stimulation based on meaningful information about head/body position (e.g. change in space and orientation) and changes thereof. Current steering is a process that is well known in the cochlear implant industry and a technique that is used in implant processing strategies. Simply put it consists of altering the electrical environment surrounding the electrode array through the activation of various patterns of cochlear implant electrodes in order to optimize the current delivery to a particular target while minimizing activation of surrounding neural elements. The term "steered" as used herein includes in its definition but is not limited to modifications of any of the stimulation properties of the electrode array (e.g. frequency, rate, level, location of stimulation) that would maximize, optimize or favour activation of the vestibular end-organs or their neural supply.

The idea of eliciting and directing non-auditory stimulation using a cochlear implant is feasible given that the inventors have previously demonstrated that while electrical stimulation through a cochlear implant device is aimed at the spiral ganglia and auditory nerve, electrical current has been confirmed to escape from the confines of the cochlea where it stimulates other sensory elements that are in close proximity. Specifically, it has been shown that electrical stimulation of the facial nerve can be detected in more than 59% of experienced cochlear implant users. In most cases facial nerve stimulation occurred at levels that were perceptually loud but comfortable.[7,8] Subclinical facial nerve stimulation, defined as the presence of a myogenic response from the facial nerve seen on electromyography in the absence of either a sensation of movement or obvious visible facial twitching occurred was seen in all subjects. On average, an initial myogenic response occurred at stimulation levels (16.4 clinical units) much below those required to produce a subjectively perceptible response or an observed twitch (22.7 clinical units). When present, myogenic responses occurred in response to electrode stimulation across the electrode array and were not limited to electrodes within a specific region. Single reports of stimulation of the vestibular end-organs via an appropriately placed intracochlear electrode array are also found in the literature.[9,10] Given the high rate of facial nerve stimulation demonstrated in the inventors' work, one might anticipate that electrical stimulation of the sensory elements associated with the vestibular end-organs may be even more common given their closer proximity to the cochlea. The challenges associated with establishing the true rate of vestibular stimulation from a cochlear implant lie in the difficulties associated with measuring this type of non-auditory stimulation. In general measuring evoked vestibular responses are not as simple or commonly performed as their auditory or facial nerve counterparts. It may also be feasible that balance gains could be achieved through the use of head referenced sub-clinical excitation of the facial or other nerves or sensory end-organs. This may be particularly relevant in children with malformed cochleovestibular anatomy and/or absent or limited cochlear and/or vestibular afferents. We also know from animal studies that when current is placed near the vestibular end-organs or perilymph (fluid filling the vestibular end-organs and cochlea) that activation of the vestibular nuclei in the brainstem occurs[11-14]. It is also known that high level acoustic stimulation can elicit in and of itself myogenic responses of the neck musculature amongst others. These responses are called the vestibular evoked myogenic potentials (VEMP). In following from this our group and others have previously demonstrated also that the myogenic responses in the neck muscles that occur through these nuclei can be elicited by the cochlear implant in a child.[9, 10, 15]

Figure 5:
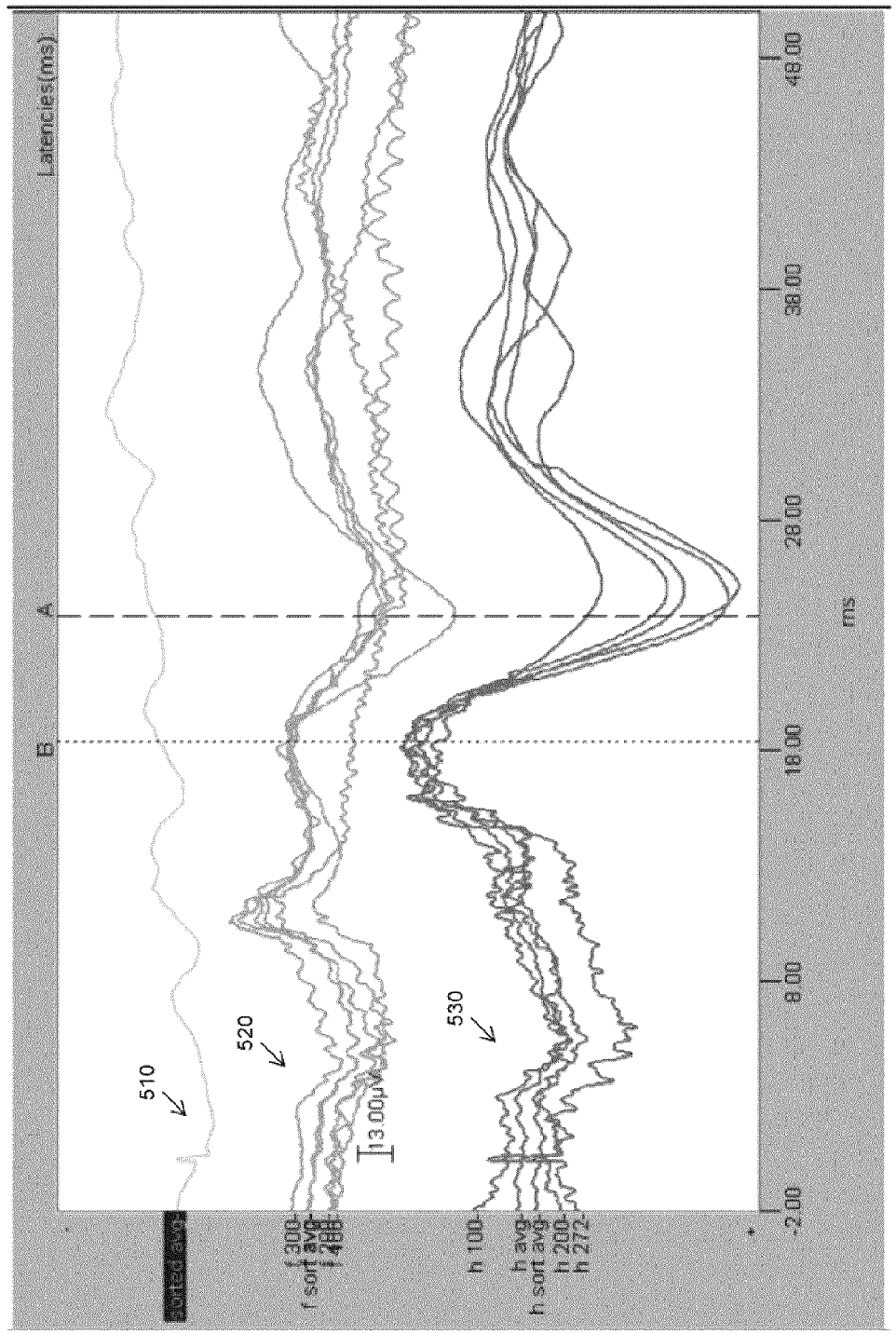
FIG. 5 illustrates electromyographic waveforms.

FIG. 5 demonstrates the classic electromyographic waveform recorded off the sternocleidomastoid muscle (SCM) of a child in response to cochlear implant activation. Multiple averaged recordings are used to validate the presence of this response. Waveform 510 represents averaged muscular activity in response to implant activation without activation of the SCM muscle, no VEMP is present. Waveform 520 represents right sided VEMP in response to electrical activation of the cochlear implant (SCM tonically activated). Waveform 530 represents left sided VEMP in response to electrical activation of the cochlear implant (SCM tonically activated). A marks the latency of the negative peak (~25 ms) and B marks the latency of the positive peak (~18 ms). Typically when evoked acoustically, VEMP responses occur with a P1 latency of 13 ms and an N1 latency of 21 ms. The longer latencies seen in the displayed waveforms may reflect delays required for electrode activation, adequate current spread and ultimately activation of the pathway through a different route.

With this in mind, some embodiments disclosed herein aim to make use of the previously used traditional hearing aids, boneconduction hearing aids or middle ear implants to provide head referenced auditory signals through an external motion processor with the overall aim of improving postural stability in the large number of patients with balance dysfunction many of whom may already use traditional hearing aids or bone conduction aids or middle ear implants.

Some embodiments disclosed herein aim to make use of the previously implanted cochlear electrode array to provide head referenced electrical impulses through an external motion processor with the overall aim of improving postural stability in the large number of patients with balance dysfunction many of whom may already have implanted cochlear stimulation devices.

Figure 6B:
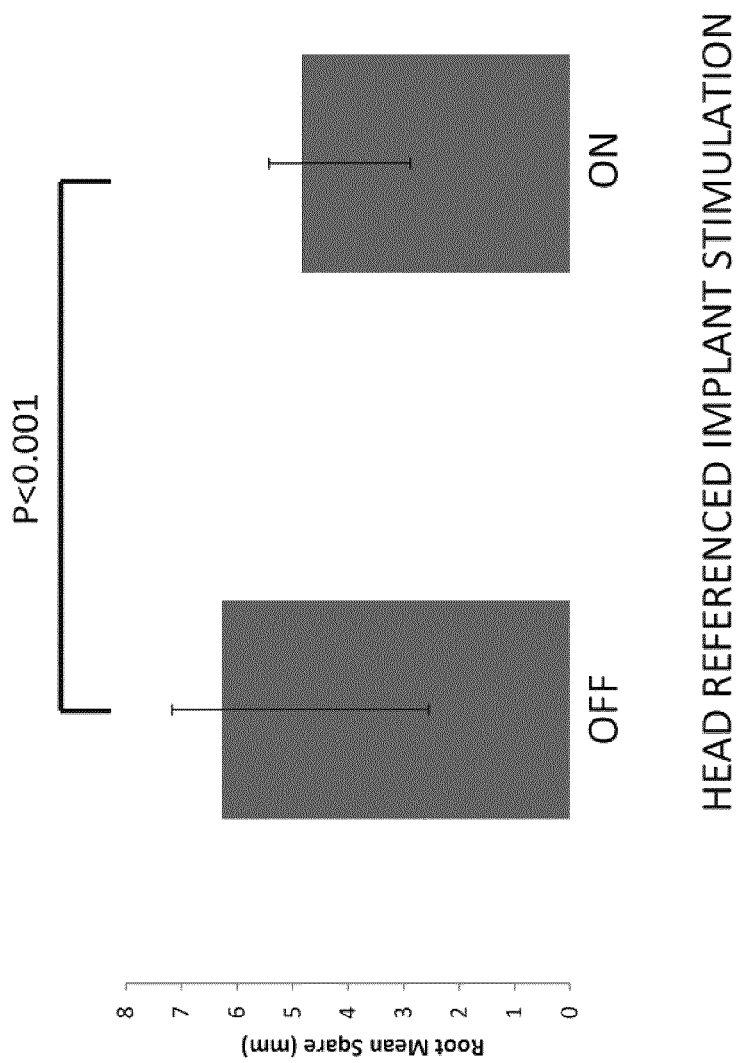
FIG. 6B illustrates boxplots of root mean square values for posturography tests.

Some embodiments disclosed herein are capable of simultaneously rehabilitating both hearing and balance deficits and in some embodiments this may be done without the need for modifications to the implanted cochlear electrode array. Specifically, some embodiments may not require implantation of a specific 'hybrid' device with electrodes directed separately at the cochlear and vestibular portions of the inner ear as described in patents '120 and '028. Various embodiments disclosed herein incorporate some of the teachings of known cochlear implant and vestibular stimulation systems exemplified by the patents previously discussed and incorporated herein by reference to provide a trans cochlear implantable stimulator that has directed speech and balance processing strategies incorporated into an external processor. Various embodiments disclosed herein encompass the novel idea of directing trans-cochlear electrical stimulation for non-auditory functions. In some embodiments, a cochlear prosthesis is enhanced with one or more balance sensors which may be one or more external spatial orientation devices (balance sensors) such as, but not limited to, rotational and linear accelerometers and gyroscopes. Signals from these balance sensors are encoded into stimuli by the cochlear prosthesis signal processor and delivered by at least one intracochlear electrode array. The electrical signals referenced to head position may selectively stimulate either the sensory epithelia of the semicircular canals and otolith centers and/or the vestibular nerve/neural elements and/or facial nerve and/or the cochlea. This stimulation may or may not elicit an associated auditory percept. Results from such an embodiment in 16 children with bilateral cochlear implants have demonstrated statistically significant improvements in measures of balance and stability (median path length/duration (p=0.01), median root mean square sway (p<0.001), falls (p=0.049)) in the presence of head-referenced stimulation of the implant FIGS. 6A and 6B illustrate the statistically significant reduction in path length/trial duration (6A) and root mean square (6B) that occurs in the presence of the stimulation system. In each of FIGS. 6A and 6B, the left boxplot corresponds to the stimulation device being off and the right boxplot corresponds to the stimulation device being on. Results in a smaller subset of this group have been published.[16]

Some embodiments of the present disclosure make use of a traditional air conduction hearing aid that is fit an external processor that allows for the provision of head reference auditory stimulation.

An example of an air conduction hearing aid system of the type currently used by many patients is described, e.g., in U.S. Pat. No. 5,719,528 which is incorporated herein by reference in its entirety. Some of the embodiments illustrated in FIG. 10 of the present application utilize components of the '528 patent along with novel elements disclosed herein.

Some embodiments of the present disclosure relate to a bone-anchored hearing aid that is fit an external processor that allows for the provision of head reference auditory stimulation.

An example of a bone conduction hearing aid system (percutaneous abutment retained) of the type currently used by many patients is fully described, e.g., in U.S. Pat. Application Publication No. 2009/0247813 which is incorporated herein by reference in its entirety. Some of the embodiments illustrated in FIG. 11 of the present application utilize components of US 2009/0247813 A1 along with novel elements disclosed herein.

Some embodiments of the present disclosure relate to a middle ear implant that is fit with an external processor that allows for the provision of head reference auditory stimulation.

An example of a middle ear implant of the type currently used by many patients is fully described, e.g., in U.S. Pat. No. 5,456,654 which is incorporated herein by reference in its entirety. Some of the embodiments illustrated in FIG. 12 of the present application utilize components of the '654 patent along with novel elements disclosed herein.

Some embodiments of the present disclosure relate to an implantable cochlear stimulating system that is fit with an external processor that allows for the provision of head reference stimulation of the intra-cochlear electrode array.

An example of a cochlear stimulation system of the type currently used by many patients is fully described, e.g., in U.S. Pat. No. 6,565,503 and U.S. Pat. No. 7,346,397 and U.S. Pat. No. 4,532,930, which are incorporated herein by reference their entireties. Some of the embodiments illustrated in FIGS. 12-16 of the present application utilize components of the '503, '397 and '930 patent along with novel elements disclosed herein.

Reference is now made to FIG. 7, which illustrates a stimulation system 700 according to various embodiments. The embodiments illustrated in FIG. 7 utilize a set of head phones 702 connected to an ear level/head mounted motion processor 704 that contains a balance sensor 706. The output of the balance sensor 706 is converted into an auditory stimulus that is routed via the headphones to the middle and inner ear. Efficacy of such an embodiment has been demonstrated in 7 adults who demonstrated statistically significant improvements in measures of balance and stability (median path length/duration (p=0.043), median root mean square sway (p=0.041) in the presence of head-referenced auditory stimulation.

Figure 8A:
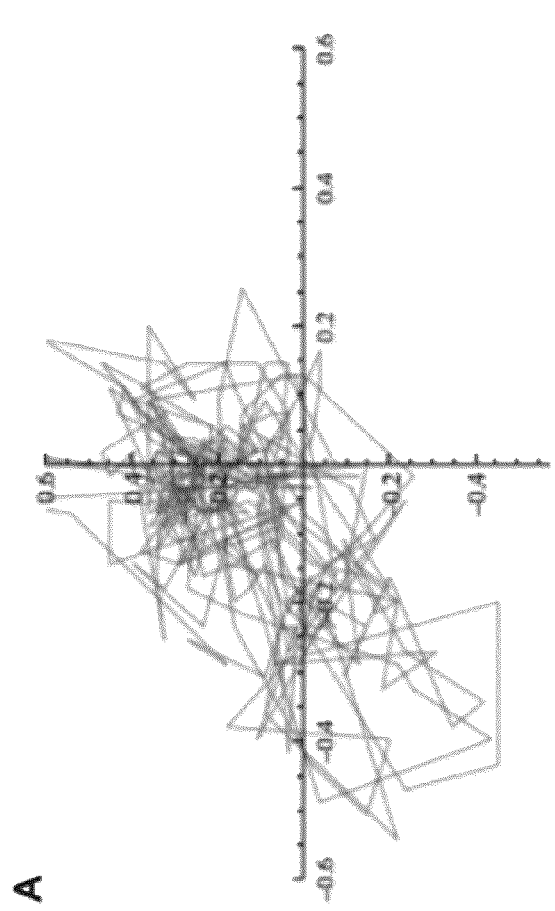
FIGS. 8A and 8B illustrate X/Y plots of head tilt.
Figure 8B:
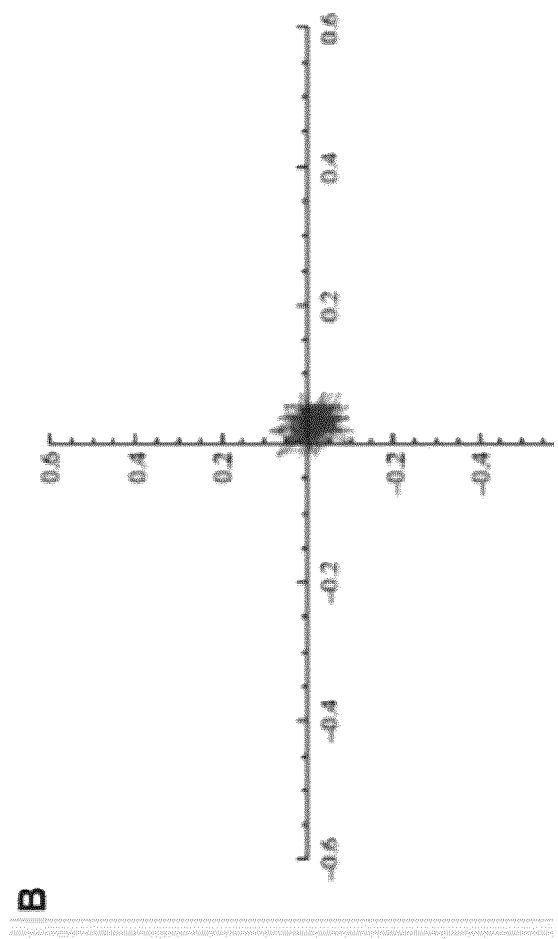

FIGS. 8A and 8B illustrate X/Y plots of head tilt. FIG. 8A shows head tilt at baseline (Stimulation off). FIG. 88 shows the reduced head tilt during use of the stimulation device. Accordingly, FIGS. 8A and 8B taken together illustrate the reduction in head tilt that occurs during use of the stimulation device.

FIG. 9A illustrates boxplots showing path length values for the sum of average posturography data for tests in each condition. The box plot on the left corresponds to the stimulation devices being off. The boxplot on the right corresponds to the stimulation device being on. FIG. 9A illustrates the reduction in path length values that occurs with utilization of the stimulation system.

Figure 9B:
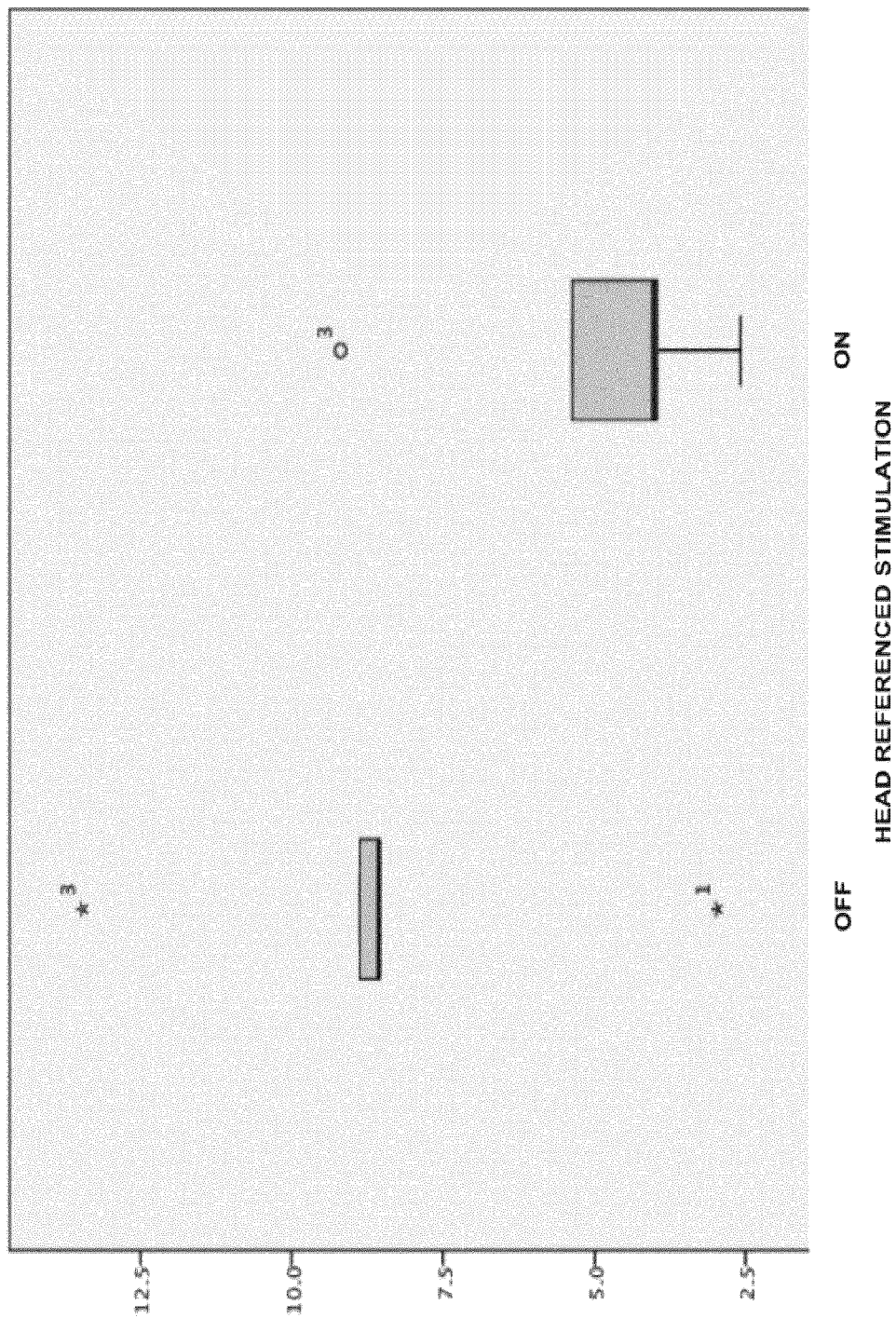
FIG. 9B illustrates boxplots of root mean square values for posturography tests.

FIG. 9B demonstrates a boxplot showing root mean square values for the sum of average posturography data for tests in each condition. The box plot on the left corresponds to the stimulation devices being off. The boxplot on the right corresponds to the stimulation device being on. FIG. 9B illustrates the significant reduction in root mean square values that occurs with utilization of the stimulation system.

Figure 10:
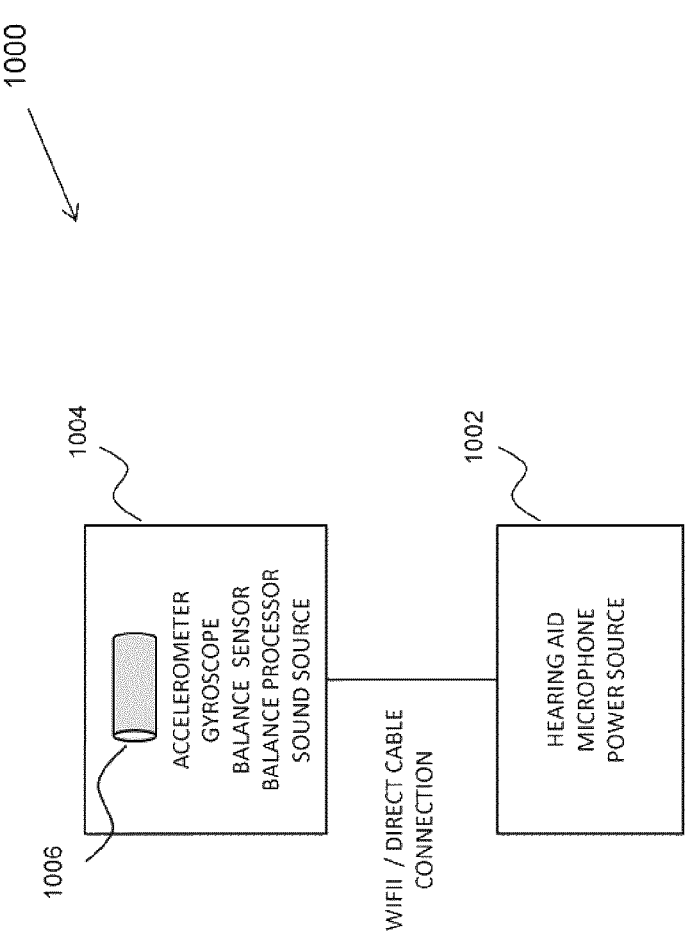
FIGS. 10 to 16 illustrate stimulation systems according to various embodiments.

Reference is now made to FIG. 10, which illustrates a stimulation system 1000 according to various embodiments. The embodiments illustrated in FIG. 10 utilize an air conduction hearing aid 1002. In various embodiments, the hearing aid 1020 includes a various components such as for example, but not limited to a power source, microphone, speech processor, various electronic circuitry such as amplifiers, and a miniature transducer. In various embodiments, the speech processor is then connected to an additional ear level motion processor 1004 that contains a balance sensor 1006. In various embodiments, the motion processor also includes a sound source, which is capable of creating an electrical signal that can be converted by the hearing aid into an auditory stimulus. The output of the balance sensor is converted into an auditory stimulus that is routed via a direct or wireless connection through the hearing aid that then leads to amplification of sound and excitation of the middle and ultimately inner ear.

Figure 11:
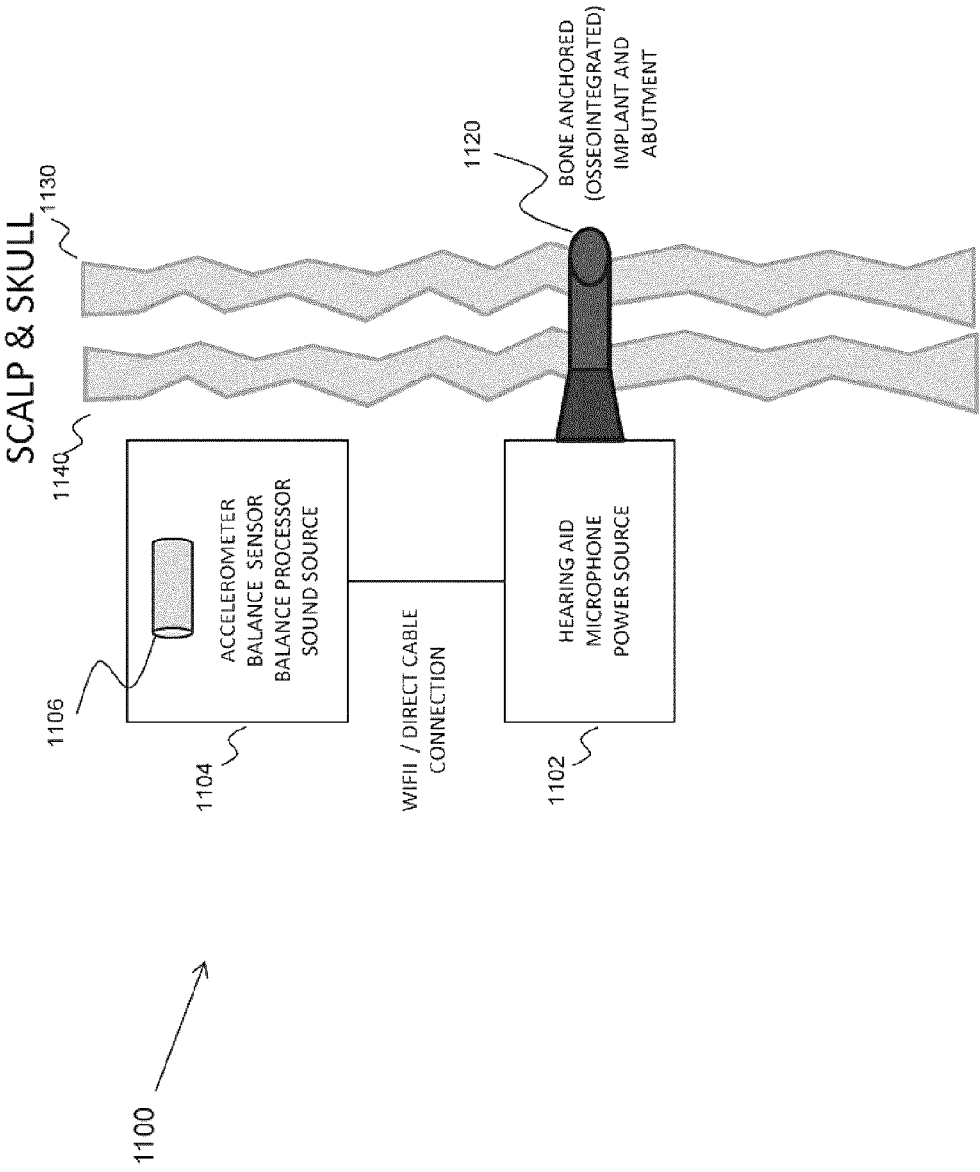

Reference is now made to FIG. 11, which illustrates a stimulation system 1100 according to various embodiments. The embodiments illustrated in FIG. 11 utilize a bone-anchored osseointegrated implant with abutment 1120. The abutment is anchored in the skull 1130 through the scalp 1140. The implant and abutment 1120 are then mechanically coupled to a bone conduction hearing aid 1120 such that vibration of the skull 1130 occurs in response to auditory stimulation. In various embodiments, the hearing aid 1120 includes a various components such as for example, but not limited to a power source, microphone, speech processor, various electronic circuitry such as and amplifiers. In various embodiments, the hearing aid 1120 is then connected to an additional ear level motion processor 1104 that contains a balance sensor 1106. In various embodiments, the motion processor also includes a sound source, which is capable of creating an electrical signal that can be converted by the hearing aid into an auditory stimulus. The output of the balance sensor 1106 is converted into an auditory stimulus that is routed via a direct or wireless connection through the hearing aid 1102 that then leads to skull vibration and an auditory percept.

Although the embodiments of FIG. 11 are described and illustrated as being coupled to the skull, there are a number of ways of coupling bone conduction hearing aids that could be used in various embodiments described herein. Other examples of bone conduction hearing aids have been mentioned above and are also applicable to various embodiments disclosed herein.

Figure 12:
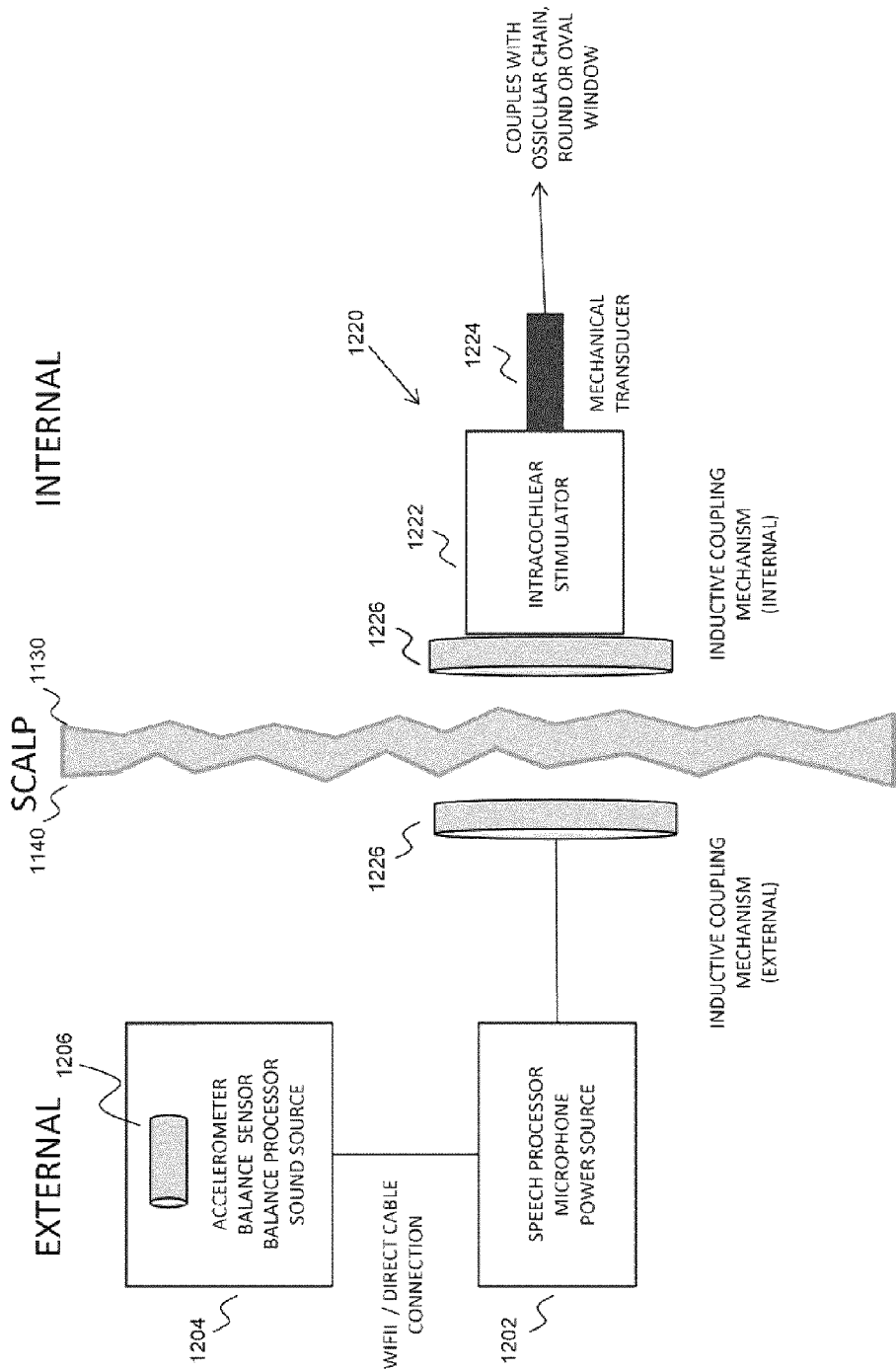

Reference is now made to FIG. 12, which illustrates a stimulation system 1200 according to various embodiments. The embodiments illustrated in FIG. 12 utilize a middle ear implant 1220 that includes an intracochlear stimulator 1222 and an implanted mechanical stimulator or transducer 1224. The mechanical transducer 1224 is coupled with the ossicular chain, round or oval window. The implant 1220 is inductively coupled (through inductive coupler 1226) with an external ear level speech processor 1202 that, in some embodiments, contains its own power source. In various embodiments, the speech processor 1202 is then connected to an additional ear level motion processor 1204 that contains a balance sensor 1206. In various embodiments, the motion processor also includes a sound source, which is capable of creating an electrical signal that can be converted by the speech processor into an auditory stimulus. The output of the balance sensor 1206 is converted into an auditory stimulus that is routed via a direct or wireless connection through the speech processor that then leads to activation of the implanted mechanical stimulator.

Figure 13:
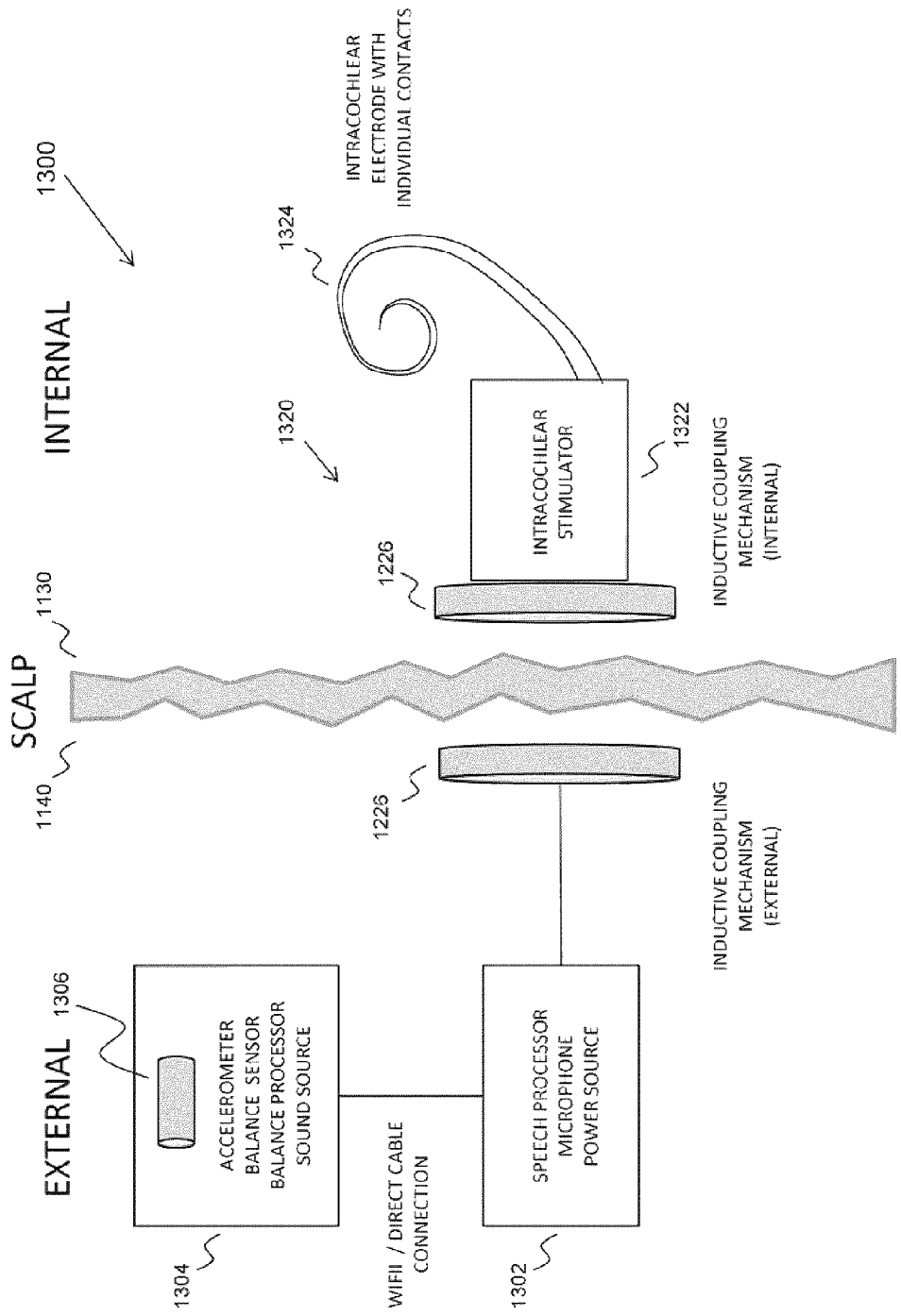

Reference is now made to FIG. 13, which illustrates a stimulation system 1300 according to various embodiments. The embodiments illustrated in FIG. 13 utilize a cochlear implant 1320 that includes an implanted cochlear stimulator 1322 and an intracochlear electrode array 1324 having individual contacts. The implant 1320 is inductively coupled (through inductive coupler 1326) with an external ear level speech processor 1302 that contains its own power source. In various embodiments, the speech processor 1302 is then connected to an additional ear level motion processor 1304 that contains a balance sensor 1306. The output of the balance sensor 1306 is converted into an auditory stimulus that is routed via a direct or wireless connection through the speech processor that then leads to activation of specific electrodes within the cochlear implant electrode array 1324.

Figure 14:
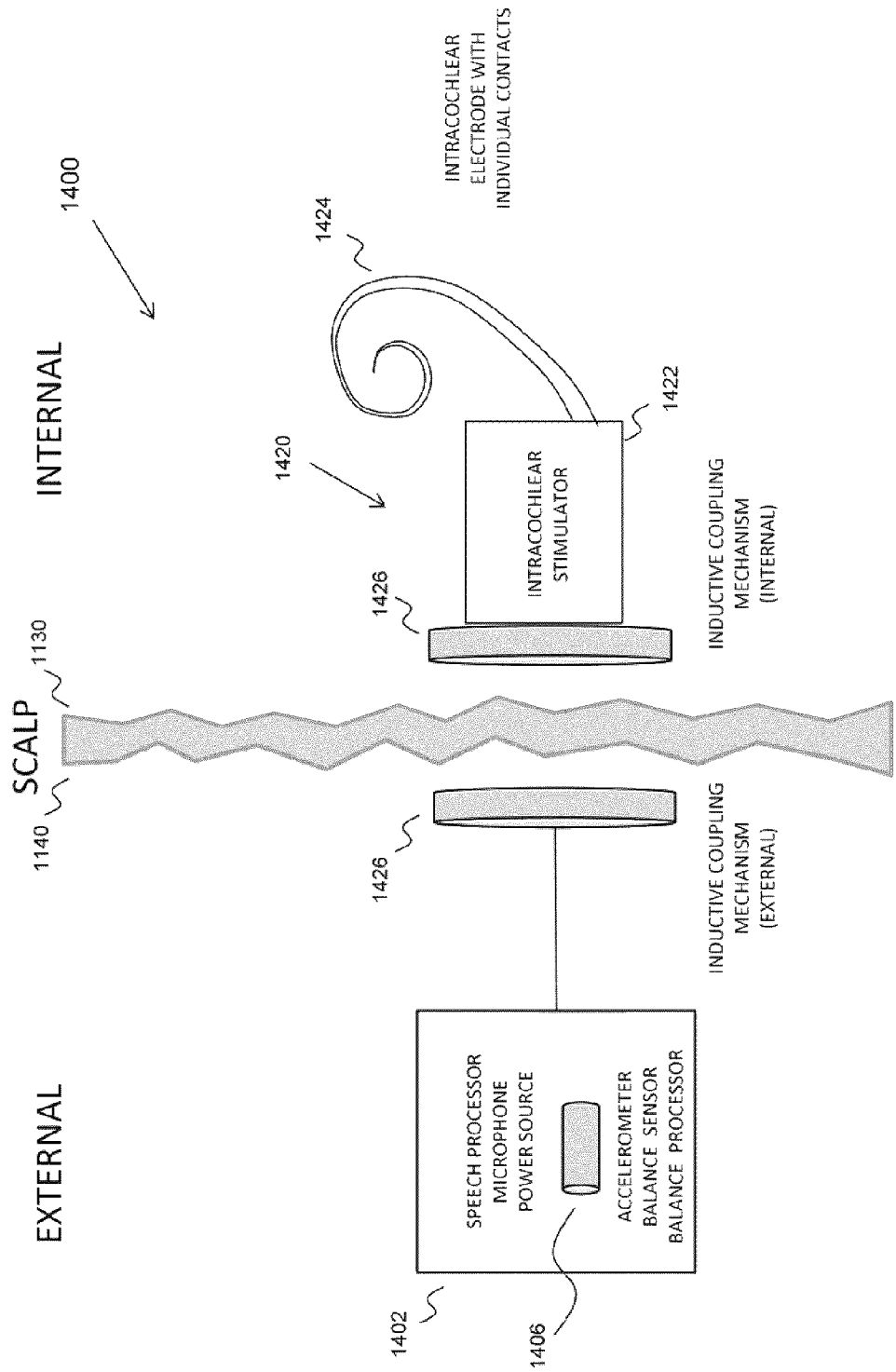

Reference is next made to FIG. 14, which illustrates a stimulation system 1400 according to various embodiments. The embodiments illustrated in FIG. 14 utilize a cochlear implant 1420 that includes an implanted cochlear stimulator 1422 and an intracochlear electrode array 1424 having individual contacts. The implant 1420 is inductively coupled with an external ear level speech processor 1402 that contains its own power source. In various embodiments, the speech processor 1402 is modified to include or be coupled to one or more balance sensors 1406. In response to changes in head/body position, the output of the balance sensor is 1406 processed and translated into electrical activation of a specific electrode(s) within the cochlear implant electrode array 1424.

Figure 15:
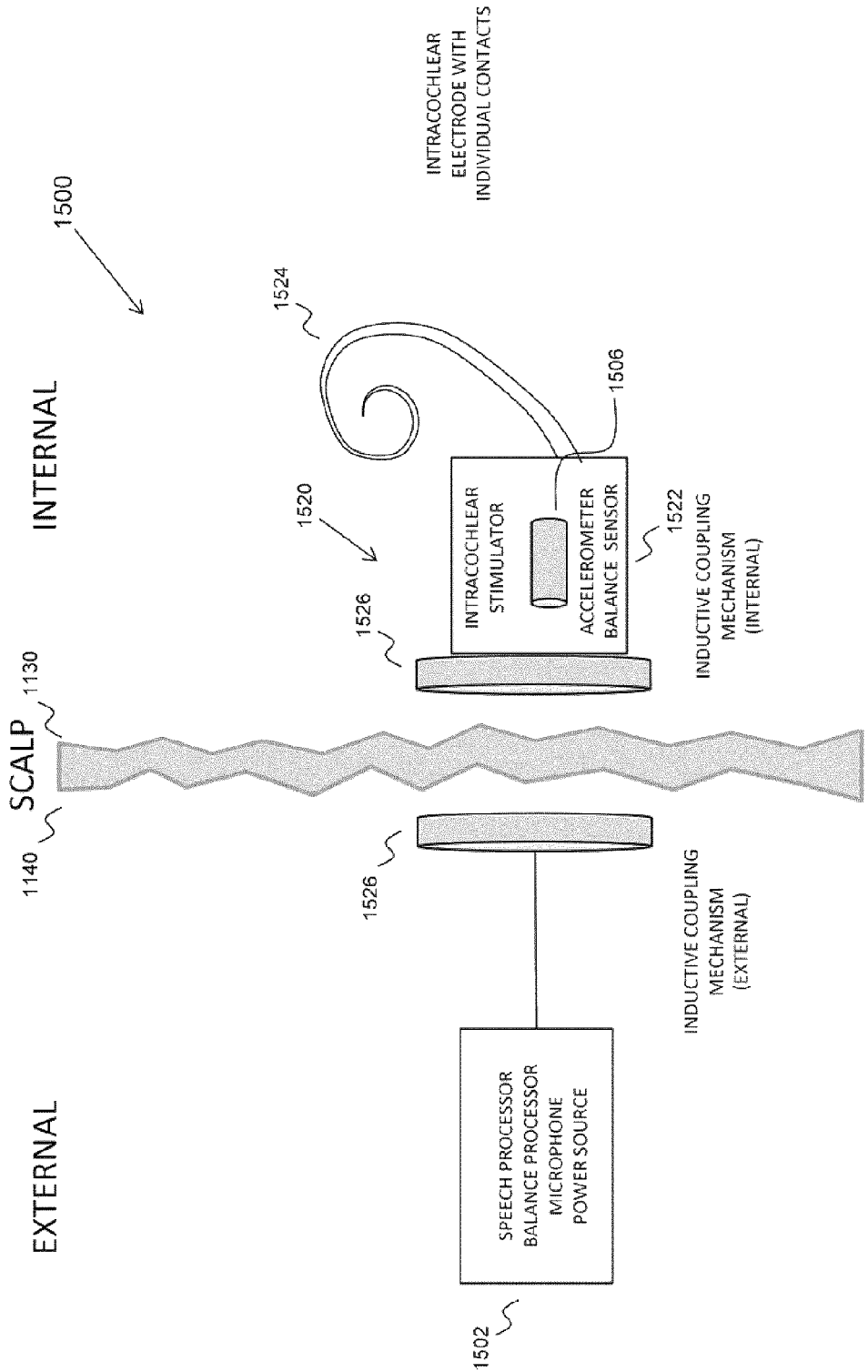

Reference is next made to FIG. 15, which illustrates a stimulation system 1500 according to various embodiments. The embodiments illustrated in FIG. 15 utilize a cochlear implant 1520 that includes an implanted cochlear stimulator 1522 and an intracochlear electrode array 1524 having individual contacts. The implant 1520 is inductively coupled with an external ear level speech and balance processor 1502 that contains its own power source. In some of the embodiments illustrated in FIG. 15, the internal cochlear stimulator is modified to contain one or more balance sensors 1506. This portion of the device which includes the internal component of inductive coupling mechanism, intracochlear stimulator 1522 and the balance sensor 1506 are head fixed. In response to changes in head/body position, the output of the balance sensor is transferred via the induction coupler and processed by the speech and balance processor 1502 and translated into electrical activation of a specific electrode(s) within the cochlear implant electrode array 1524.

Figure 16:
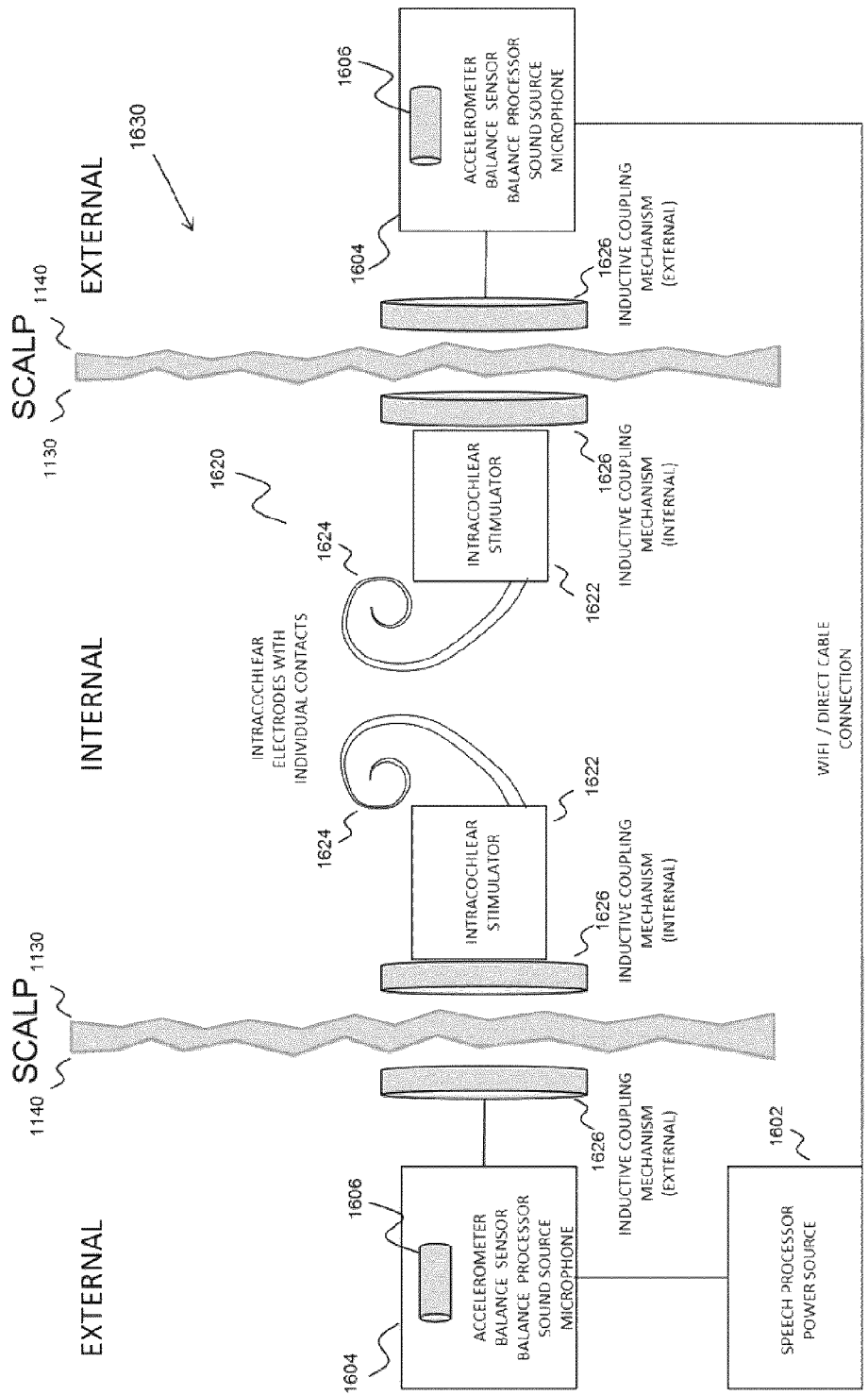

Reference is next made to FIG. 16, which illustrates a stimulation system 1600 according to various embodiments. The embodiments illustrated in FIG. 16 utilize a cochlear implant 1620 that includes an implanted cochlear stimulator 1622 and an intracochlear electrode array 1624 having individual contacts. The implant 1620 is inductively coupled with an external ear level speech processor that contains its own power source. In the embodiments illustrated in FIG. 16, the patient has bilateral cochlear implants. In some embodiments, a single speech processor 1602 is connected to bilateral ear level balance processors 1604 that contains the device microphone and the balance sensors 1606. The output of the balance sensors are converted into an auditory stimulus that is routed via a direct or wireless connection through the single speech processor which then leads to coordinated activation of specific electrodes within the bilateral cochlear implant electrode arrays 1624.

As used herein, the term "balance sensor" refers to any sensor (or combination of sensors) that can be used to determine one or more balance characteristics of a patient, including but not limited to, a sensor that senses motion (including but not limited to acceleration or velocity), position, gravity, rotation, orientation, video, magnetic North and geopositioning of the head and/or body. Accordingly, the term balance sensor, as used herein, can refer to any position, motion, or orientation sensor or any combination of one or more position, motion, or orientation sensor (e.g. some embodiments utilize accelerometers and gyroscopes in combination). The term position, as used herein, refers to changes in space (e.g. relative location), orientation or changes in both space and orientation. Some embodiments disclosed herein utilize multiple balance sensors. The sensors can be, for example, but are not limited to, lightweight accelerometers, such as those discussed, for example, in the '578 patent and lightweight body sway sensors such as velocity transducers or sensors as described throughout the '046 and '149 patents, micro-electro-mechanical systems (MEMS), piezo-electric accelerometers, gyroscopes, digital compass, augmented/differential global positioning system receiver, or other rotation and/or linear accelerometers may be used. In various embodiments, the balance sensors can be of any suitable type. In some embodiments, a combination of different types can be used in the same embodiment (e.g. a given embodiment may utilize accelerometers and position sensors).

In some embodiments, the balance sensors are included within the unit or are mounted to the case of the unit. In various embodiments, the sensors may include rotation sensors oriented to a sense of patient's pitch and roll axis as described in the '291 patent. These sensors may either be aligned as in the '291 patents which require the placement of 3 rotational accelerometers in mutually orthogonal cardinal X, Y and Z planes to measure roll, pitch and yaw of the head, or aligned with the semicircular canals or otolith planes of the implanted patient (or the mean position of human semicircular canal planes) as proposed in patents '120 and '028. In some embodiments, a dynamic alignment may also be possible offering a device that could be zeroed once the device is in place and the patient's head is in the zeroing positioning. In some embodiments, only two planes will be represented initially in an effort to reduce the computational demands of the device and ultimately power consumption while minimizing interference with hearing. In some embodiments, additional sensors responding to yaw or translational movements may be included later.

The systems shown in FIGS. 13 and 16 includes implanted and external components. The external components include a speech and/or motion processor, a power source (e.g. a replaceable battery) and at least one orientation/balance sensor. In some embodiments, the internal components are comprised of an industry standard cochlear implant. The sensor(s) is (are) housed either in or outside of the processor and may sit at ear level. When not housed within the processor the balance sensor(s) are coupled to it via any suitable connection, including, but not limited to, a direct cable, WiFi (IEEE 802.11), Bluetooth (IEEE 802.15), ZigBee (IEEE 802.15.4) or other wireless connection. In summary, the processor, power source and the motion processor may be housed within a wearable unit or housed in separate units that communicate via, direct cable, RF or other suitable wireless link. In some of the embodiments illustrated in FIGS. 11 to 16, the implanted components could remain unchanged from previously implanted systems/devices, which may include, for example, the devices taught in the previously referenced patent documents. Single or multiple intra-cochlear electrode(s) within the array may be used to respond to head-referenced motion.

Some embodiments described herein utilize components that have already been implanted. In some such embodiments, balance sensors are provided and the speech processor is replaced with one or more processors so that stimulation signals to correct balance disorders can be provided in addition to the stimulation signals that correct for hearing disorders. Accordingly, in some embodiments, some existing systems for treating hearing disorders, which include an implanted portion and an external portion, can be modified to also treat some balance disorders. In some cases, such systems can be modified without operating on a patient to modify the implanted portion. Accordingly, in some cases where the existing system includes an external processor (e.g. a speech processor) for providing control signals based on sensed audio information, the system can be modified in a manner that is not invasive to a patient by providing balance sensors and by replacing, modifying, or supplementing the speech/sound processor to also account for balance information.

In FIG. 14, the implanted portion of the cochlear implant is modified to incorporate the balance sensor(s) internally and support them in a head fixed position. Output of the balance sensors is then relayed via the induction coupling mechanism to the speech and motion processor and re-relayed back to the internal stimulator ultimately leading to selective activation of the intra-cochlear electrode array.

In use, a carrier signal is generated by circuitry within the wearable external unit using energy derived from the power source within the speech processor unit. Such a carrier signal, which is an AC signal, is conveyed over the cable to the headpiece where it is inductively coupled to the coil within the implanted cochlear stimulator. There it is rectified and filtered and provides a DC power source for operation of the circuitry within the implanted cochlear stimulator. Sounds are sensed through the microphone and movements, acceleration, gravity and/or orientation are sensed through the balance sensors. The information, sensed by the microphone and sensors, is processed by circuitry included either within or external to the processor unit and converted to appropriate stimulation signals in accordance with a selected speech and balance processing strategy by circuitry within the sound and/motion processor unit. These stimulation signals modulate the carrier signal that transfers power to the implanted cochlear stimulator. The implanted cochlear stimulator includes an appropriate demodulation circuit that recovers the stimulation signals from the modulated carries and applies them to individual or a plurality of electrodes within the electrode array. The stimulation signals identify which electrode(s), or electrode pairs, are to be stimulated, the sequence of stimulation and the intensity of the stimulation.

In some embodiments, when adjustment or fitting or other diagnostic routines need to be carried out, an external programming unit is detachably connected to the speech and motion processor. In various embodiments where an external processor is utilized, through the use of the external processor, a clinician or other medical personnel is able to select the best speech and motion processing strategies for the patient, as well as set other variables associated with the stimulation process.

In various embodiments, the batteries employed within the speech and/or motion processor may be readily replaced when needed. When the processor unit is removed, the cochlear and/or vestibular stimulation will cease. This may lead to a decrement in balance when the device is off or even percepts of vertigo or motion.

Balance or other sensors of various embodiments disclosed herein not located with the body may include those discussed by the patents incorporated herein by reference. In various embodiments, balance sensors may be replaced and/or accompanied by externally worn balance sensors. At the outset it should be noted that the present disclosure is not directed, per se, to the specific electronic circuitry or electronic components used or housed within each of these modules. Any type of suitable circuitry could be used in the modules that perform the functions indicated. Circuitry and components suitable for these purposes are disclosed, e.g. in the referenced patents. The present disclosure, rather, is directed to systems that combine the indicated modules the various manners to form some of the embodiments described herein. Some of the embodiments described herein provide at least one of the advantages and benefits enumerated herein, which advantages and benefits have not heretofore been available. However, not all embodiments are directed to or include the advantages listed and enumerated herein. Some embodiments have other advantages that are not described herein.

Humans have two vestibular labyrinths, one in each ear that co-operate with each other to provide balance information to the central nervous system. The present disclosure may be practiced in a variety of unilateral, bilateral or multilateral embodiments. FIG. 16 displays various embodiments where a single speech and/or motion processor is used to process the information captured bilaterally at the level of the ear level microphone and balance sensor. In some embodiments the bilateral input is synchronized and delivered via the induction coupling mechanisms simultaneously to both intracochlear stimulators.

In various embodiments, the speech and/or speech/balance processor of the present disclosure may be configured to provide auditory cues or feedback indicative of the patient's spatial orientation or velocity through existing cochlear electrode arrays such as that described in, for example, in U.S. Pat. No. 5,597,380. Auditory feedback is described in further detail above and in the '046 and '149 patents, the teachings of which, as with the teachings of all other patents mentioned throughout this specification are incorporated herein by reference.

As described above, it is further seen that one or more embodiments of the present disclosure provide head referenced electrical stimulation of the implantable intracochlear electrode array capable of stimulating proper auditory and/or vestibular sensations to the brain of a patient yielding the outcome of improved static and dynamic balance. Thus a patient (depending at least in part on his/her medical condition) using one of the embodiments of the present disclosure may benefit through the use of restored hearing and proper balance and orientation.

It should be understood that various embodiments disclosed herein, such as those illustrated in FIGS. 13 to 16 can be used to provide balance based stimulation that is not perceptible to the patient. For example, the balance based stimulation may be provided by electrical impulses that are steered towards the vestibular nerve or alternatively applied directly to the vestibular nerve.

It should be understood that the 'speech processor' referenced in the above embodiments and in FIGS. 13 to 16 can be used to process balance related information and can have the capacity to provide stimulation of the implanted cochlear electrode array that is steered toward the vestibular end-organs or their neural elements in a fashion that is independent of the processing strategies for external auditory stimuli.

As described above, it is further seen that one or more embodiments of the present disclosure may be used as a training or rehabilitation device where a patient could use the device for a given duration of time, and potentially repeated over time, and may receive a sustained positive effect on balance.

While the teachings of the present disclosure herein disclosed have been described by means of specific embodiments and applications thereof, numerous modifications and variations could be made thereto by those skilled in the art without departing from the scope of the invention set forth in the claims.

APPENDIX

List of References Cited

Each of the references listed herein is incorporated herein by reference in its entirety.

1. Buchman C A, Joy J, Hodges A, Telischi F F, Balkany T J. Vestibular effects of cochlear implantation. *Laryngoscope*. October 2004; 114(10 Pt 2 Suppl 103):1-22.
2. Cushing S L, Chia R, James A L, Papsin B C, Gordon K A. A test of static and dynamic balance function in children with cochlear implants: the vestibular olympics. *Arch Otolaryngol Head Neck Surg*. January 2008; 134(1):34-38.
3. Cushing S L, Gordon K A, Rutka J A, James A L, Papsin B C. Vestibular End-Organ Dysfunction in Children With Sensorineural Hearing Loss and Cochlear Implants: An Expanded Cohort and Etiologic Assessment. *Otol Neurotol*. January 30.
4. Cushing S L, Papsin B C, Rutka J A, James A L, Blaser S L, Gordon K A. Vestibular end-organ and balance deficits after meningitis and cochlear implantation in children correlate poorly with functional outcome. *Otol Neurotol*. June 2009; 30(4):488-495.
5. Cushing S L, Papsin B C, Rutka J A, James A L, Gordon K A. Evidence of vestibular and balance dysfunction in children with profound sensorineural hearing loss using cochlear implants. *Laryngoscope*. October 2008; 118(10) 1814-1823.

6. Firszt J B, Koch D B, Downing M, Litvak L. Current steering creates additional pitch percepts in adult cochlear implant recipients. *Otol Neurotol*. August 2007; 28(5):629-636.
7. Cushing S L, Papsin B C, Gordon K A. Incidence and characteristics of facial nerve stimulation in children with cochlear implants. Laryngoscope. October 2006; 116(10) 1787-1791.
8. Cushing S L, Papsin B C, Strantzas S, Gordon K A. Facial nerve electromyography: a useful tool in detecting nonauditory side effects of cochlear implantation. *J Otolaryngol Head Neck Surg*. April 2009; 38(2):157-165.
9. Jin Y, Nakamura M, Shinjo Y, Kaga K. Vestibular-evoked myogenic potentials in cochlear implant children. *Acta Otolaryngol*. February 2006; 126(2):164-169.
10. Jin Y, Shinjo Y, Akamatsu Y, et al. Vestibular evoked myogenic potentials evoked by multichannel cochlear implant—influence of C levels. *Acta Otolaryngol*. March 2008; 128(3):284-290.
11. Cushing S. Bui T, Rose P K. Effect of nonlinear summation of synaptic currents on the input-output properties of spinal motoneurons. *J Neurophysiol. November* 2005; 94(5):3465-3478.
12. Ezure K, Cohen M S, Wilson V J. Response of cat semicircular canal afferents to sinusoidal polarizing currents: implications for input-output properties of second-order neurons. *J Neurophysiol*. March 1983:49(3):639-648.
13. Precht W, Shimazu H. Functional connections of tonic and kinetic vestibular neurons with primary vestibular afferents. *J Neurophysiol*. November 1965; 28(6):1014-1028.
14. Rose P K, Cushing S. Relationship between morphoelectrotonic properties of motoneuron dendrites and their trajectory. *J Comp Neurol*. Jun. 7 2004; 473(4):562-581.
15. Jin Y, Shinjo Y. Akamatsu Y, Yamasoba T, Kaga K. Vestibular evoked myogenic potentials of children with inner ear malformations before and after cochlear implantation. *Acta Otolaryngol*. November 2009; 129(11):1198-1205.
16. Cushing S L, Pothier D, Hughes C, Hubbard B J, Gordon K A, Pepsin B C. Providing auditory cues to improve stability in children who are deaf. *Laryngoscope*. December; 122 Suppl 4:S101-102.

What is claimed is:

1. A stimulation system comprising:
an implantable cochlear stimulator comprising:
a pulse generator that generates electrical stimulation pulses as defined by control signals; and
an intracochlear electrode array adapted to be inserted into a patient's cochlea and provide electrical stimulation pulses, comprising both auditory stimulation pulses based on audio information and balance stimulation pulses based on balance information, to the patient's auditory nerve based on the control signals;
at least one microphone configured to sense and provide audio information;
at least one balance sensor configured to sense and provide the balance information; and
at least one processor configured to generate the control signals in response to the sensory information provided by the at least one microphone and the balance information provided by the at least one balance sensor,
such that non-auditory stimulation comprising the balance stimulation pulses are provided within the cochlea for indirectly providing electrical stimulation pulses to at least one of a patient's vestibular nerve, end organs, or neural elements.

2. The stimulation system of claim 1, wherein the balance sensor is head-referenced.
3. The stimulation system of claim 2, wherein the balance sensor is adapted to be implanted into the patient's skull.
4. The stimulation system of claim 1, wherein the balance stimulation pulses are steered towards the patient's vestibular nerve/end-organs/neural elements.
5. The stimulation system of claim 1, wherein the balance stimulation pulses are steered towards the patient's facial nerve.
6. The stimulation system of claim 1, wherein the at least one processor is configured to generate the control signals for directing/steering the balance stimulation pulses towards the at least one of the patient's vestibular nerve, end-organs, or neural elements.

7. A stimulation system comprising:
an implantable cochlear stimulator comprising:
a pulse generator that generates electrical stimulation pulses as defined by control signals; and
an intracochlear electrode array adapted to be inserted into a patient's cochlea and provide electrical stimulation pulses, comprising both auditory stimulation pulses based on audio information and balance stimulation pulses based on balance information, to the patient's auditory nerve based on the control signals;
at least one balance sensor configured to sense and provide the balance information; and
at least one processor configured to generate the control signals in response to the balance information provided by the at least one balance sensor, and to provide the control signals to the implantable cochlear stimulator,
such that non-auditory stimulation comprising the balance stimulation pulses are provided within the cochlea for indirectly providing electrical stimulation pulses to at least one of a patient's vestibular nerve, end organs, or neural elements.

8. The stimulation system of claim 7, wherein the balance sensor is head-referenced.
9. The stimulation system of claim 8, wherein the balance sensor is adapted to be implanted into the patient's skull.
10. The stimulation system of claim 7, wherein the balance stimulation pulses are steered towards the patient's vestibular nerve/end-organs/neural elements.
11. The stimulation system of claim 7, wherein the balance stimulation pulses are steered towards the patient's facial nerve.
12. The stimulation system of claim 7, wherein the at least one processor is configured to generate control signals for steering the balance stimulation pulses towards the patient's vestibular nerve/end-organs/neural elements.

13. A stimulation system for use with a pulse generator that generates electrical stimulation pulses as defined by control signals and an intracochlear electrode array inserted into a patient's cochlea to provide the electrical stimulation pulses, the stimulation system comprising:
at least one microphone configured to sense and provide audio information;
at least one balance sensor configured to sense and provide balance information; and
at least one processor configured to generate control signals in response to the audio information provided by the at least one microphone and the balance information provided by the at least one balance sensor, wherein the control signals are utilized by the pulse generator to provide both auditory stimulation pulses based on the audio information and balance stimulation pulses based on the balance information, such that non-auditory stimulation comprising the balance stimulation pulses are provided within the cochlea for indirectly providing electrical stimulation pulses to at least one of a patient's vestibular nerve, end organs, or neural elements.

* * * * *